(12) United States Patent
Navratil et al.

(10) Patent No.: US 10,687,781 B2
(45) Date of Patent: Jun. 23, 2020

(54) HEMODYNAMIC MONITORING DEVICE AND METHODS OF USING SAME

(71) Applicant: Nilus Medical LLC, Redwood City, CA (US)

(72) Inventors: Miroslav Navratil, Jihlava (CZ); Karel Zadrobilek, Hradec Kralove (CZ); Jan Belohlavek, Beroun (CZ); Tomas Kovarnik, Prague (CZ); Mikulas Mlcek, Prague (CZ); Marek Santavy, Brno (CZ); Vladimir Vasek, Lelekovice (CZ)

(73) Assignee: Nilus Medical LLC, Redwood City, CA (US)

( * ) Notice: Subject to any disclaimer, the term of this patent is extended or adjusted under 35 U.S.C. 154(b) by 816 days.

(21) Appl. No.: 14/776,577

(22) PCT Filed: Mar. 14, 2014

(86) PCT No.: PCT/US2014/027133
§ 371 (c)(1),
(2) Date: Sep. 14, 2015

(87) PCT Pub. No.: WO2014/152260
PCT Pub. Date: Sep. 25, 2014

(65) Prior Publication Data
US 2016/0029995 A1   Feb. 4, 2016

Related U.S. Application Data

(60) Provisional application No. 61/952,679, filed on Mar. 13, 2014, provisional application No. 61/889,442, (Continued)

(51) Int. Cl.
*A61B 5/08* (2006.01)
*A61B 8/06* (2006.01)
(Continued)

(52) U.S. Cl.
CPC ............ *A61B 8/06* (2013.01); *A61B 5/02028* (2013.01); *A61B 5/0402* (2013.01); *A61B 5/08* (2013.01);
(Continued)

(58) Field of Classification Search
CPC .... A61B 8/06; A61B 8/12; A61B 8/54; A61B 8/463; A61B 8/5207; A61B 8/0891;
(Continued)

(56) References Cited

U.S. PATENT DOCUMENTS

| 4,319,580 A | 3/1982 | Colley et al. |
| 5,183,040 A | 2/1993 | Nappholz et al. |

(Continued)

FOREIGN PATENT DOCUMENTS

WO    2012/064769    5/2012

OTHER PUBLICATIONS

Applicant, Reply to the European Patent Office Outstanding Office Letter for Application No. 14767338.8, dated Apr. 5, 2017.
(Continued)

*Primary Examiner* — Navin Natnithithadha
*Assistant Examiner* — Andrey Shostak
(74) *Attorney, Agent, or Firm* — Dunlap Codding, P.C.

(57) ABSTRACT

Hemodynamic monitoring systems and methods are disclosed including a device comprising a first sensor configured to measure a velocity of blood flow in an adjacently-located portion of a superior vena cava of a mammalian patient using ultrasound waves; a second sensor configured to measure respiratory cycle data of the mammalian patient; and a computer configured to process the measured velocity of blood flow and the measured respiratory cycle data to provide hemodynamic parameters corresponding to the mammalian patient.

15 Claims, 16 Drawing Sheets

Related U.S. Application Data filed on Oct. 10, 2013, provisional application No. 61/788,883, filed on Mar. 15, 2013.

(51) Int. Cl.

| | |
|---|---|
| *A61B 8/08* | (2006.01) |
| *A61B 5/02* | (2006.01) |
| *A61B 5/0402* | (2006.01) |
| *A61B 5/00* | (2006.01) |
| *A61B 8/12* | (2006.01) |
| *A61B 8/00* | (2006.01) |
| *A61B 5/026* | (2006.01) |
| *A61B 5/0452* | (2006.01) |

(52) U.S. Cl.
CPC .......... *A61B 5/0803* (2013.01); *A61B 5/0809* (2013.01); *A61B 5/0816* (2013.01); *A61B 5/7278* (2013.01); *A61B 5/7405* (2013.01); *A61B 5/7425* (2013.01); *A61B 8/0891* (2013.01); *A61B 8/12* (2013.01); *A61B 8/463* (2013.01); *A61B 8/488* (2013.01); *A61B 8/5207* (2013.01); *A61B 8/5223* (2013.01); *A61B 8/54* (2013.01); *A61B 5/0261* (2013.01); *A61B 5/0452* (2013.01); *A61B 8/5284* (2013.01); *A61B 2562/0247* (2013.01)

(58) Field of Classification Search
CPC ..... A61B 8/5223; A61B 8/488; A61B 8/5284; A61B 5/0402; A61B 5/0803; A61B 5/0809; A61B 5/0816; A61B 5/7278; A61B 5/7405; A61B 5/7425; A61B 5/08; A61B 5/02028; A61B 5/0452; A61B 5/0261; A61B 2562/0247

See application file for complete search history.

(56) References Cited

U.S. PATENT DOCUMENTS

| | | | |
|---|---|---|---|
| 6,612,989 B1 | 9/2003 | Brock-Fisher | |
| 2003/0216621 A1* | 11/2003 | Alpert | ................. A61B 5/0215 600/300 |
| 2004/0127798 A1* | 7/2004 | Dala-Krishna | ........ A61B 8/065 600/450 |
| 2009/0076345 A1* | 3/2009 | Manicka | .............. A61B 5/0205 600/301 |
| 2009/0099424 A1 | 4/2009 | O'Brien et al. | |
| 2009/0137917 A1 | 5/2009 | Goedje et al. | |
| 2009/0177090 A1 | 7/2009 | Grunwald | |
| 2009/0216140 A1* | 8/2009 | Skrabal | .............. A61B 5/02028 600/509 |
| 2010/0036253 A1* | 2/2010 | Vezina | ............... A61B 5/02028 600/453 |
| 2011/0004099 A1 | 1/2011 | Kim | |
| 2011/0144967 A1 | 6/2011 | Adirovich | |
| 2011/0270111 A1* | 11/2011 | Cannesson | .......... A61B 5/0456 600/521 |
| 2012/0136242 A1* | 5/2012 | Qi | ......................... A61B 5/026 600/424 |
| 2012/0179135 A1 | 7/2012 | Rinehart et al. | |
| 2012/0296216 A1* | 11/2012 | Sharf | ................... A61B 8/4209 600/454 |
| 2013/0137987 A1* | 5/2013 | Abe | ..................... A61B 8/0883 600/454 |
| 2013/0296693 A1 | 11/2013 | Wenzel | |
| 2013/0317322 A1* | 11/2013 | Andrijauskas | ..... A61B 5/14546 600/309 |

OTHER PUBLICATIONS

PCT/US2014/027133—WO/2014/152260—International Search Report and Written Opinion—dated Aug. 22, 2014.

European Patent Office, European Search Opinion for Application No. 14767338.8, dated Sep. 21, 2016.

European Patent Office, Supplementary European Search Report for Application No. 14767338.8, dated Sep. 12, 2016.

Communication Pursuant to Article 94(3) EPC regarding Rejection from the European Patent Office for Patent Application No. 14767338.8, dated Nov. 19, 2018.

Response to Nov. 19, 2018 Communication Pursuant to Article 94(3) EPC for European Patent Application No. 14767338.8, dated Mar. 22, 2019.

International Search Report and Written Opinion for PCT Application No. PCT/US2014/027133, dated Aug. 22, 2014.

\* cited by examiner

HEMODYNAMIC MONITORING DEVICE AND METHODS OF USING SAME

INCORPORATION BY REFERENCE OF RELATED APPLICATIONS

The present patent application is a national stage application filed under 35 U.S.C. 371 of PCT/US2014/027133, filed Mar. 14, 2014; which claims priority to the provisional patent applications identified by U.S. Ser. No. 61/788,883 titled "HEMODYNAMIC MONITORING DEVICE AND METHODS OF USING SAME" filed on Mar. 15, 2013, U.S. Ser. No. 61/889,442 titled "HEMODYNAMIC MONITORING DEVICE AND METHODS OF USING SAME" filed on Oct. 10, 2013, and U.S. Ser. No. 61/952,679 titled "HEMODYNAMIC MONITORING DEVICE AND METHODS OF USING SAME" filed on Mar. 13, 2014, the entire contents of which are hereby incorporated herein by reference.

BACKGROUND

1. Field of the Inventive Concept(s)

The presently disclosed and/or claimed inventive concept(s) relates generally to a hemodynamic monitoring device and methods of making and using same. The hemodynamic monitoring device and its use are particularly well-suited for the measurement of respiratory cycle data simultaneously with at least one of central venous blood pressure and intravascular blood flow velocity and thereafter correlating these measurements to monitor mammalian patients such as humans. In particular, but without limitation, the hemodynamic monitoring device is capable of providing data and information correlating to a fluid responsiveness of the mammalian patient on a continuing basis and in real-time. In one specific but non-limiting embodiment, the respiratory cycle data of the mammalian patient is correlated with at least one of velocity of blood flow in the superior vena cava and central venous blood pressure in order to provide data and information that is thereby calculated and correlated with the fluid responsive state of the patient. In one specific but non-limiting embodiment, the respiratory cycle data of the mammalian patient is correlated with at least one of velocity of blood flow in the superior vena cava in order to provide data and information that is thereby calculated and correlated with the level of right ventricle dysfunction and/or acute pulmonary hypertension in the patient. The hemodynamic device includes sensors to minimally invasively measure the velocity of blood flow in the superior vena cava, central venous blood pressures, and the respiratory cycle data of the patient.

2. Background of the Inventive Concept(s)

Hemodynamic monitoring is a central aspect of cardiovascular diagnosis and titration of care. For example, circulatory shock results primarily in inadequate tissue blood flow. Although most forms of shock may show some increase in cardiac output initially in response to fluid loading, it has been estimated that at least fully one-half of all hemodynamically unstable intensive care unit patients are not preload responsive. See, e.g., Michael, F. et al., "Predicting fluid responsiveness in ICU patients: a critical analysis of the evidence," Chest 2002; 121:2000-2008, the entire contents of which are hereby incorporated by reference in their entirety. As such, the following fundamental question confronts intensive care providers on a daily basis: will fluid improve perfusion to end organs, or will it cause fluid overload and worsen pulmonary or systemic edema? For example, when treating septic patients volume expansion is often one of the cornerstones of early resuscitation. Volume overload ("hypervolemia") can have dire consequences such as decreased gas exchange and increased myocardial dysfunction.

A reduction in intravascular volume results in a fall in stroke volume, which is initially compensated for by an increase in heart rate thereby maintaining cardiac output. However, with further volume depletion cardiac output and then blood pressure falls. This is associated with a reduction in organ perfusion. At the organ level, the local autoregulatory mechanism attempts to maintain tissue perfusion.

The patient's hemodynamic state can oftentimes rapidly change as it is influenced by a host of intertwined and interdependent factors. Several studies suggest, for example, that even experienced intensivists using traditional parameters are correct only about half of the time when determining preload responsiveness. As such, static measurements or indices of fluid responsiveness, such as the traditionally used tests of central venous pressure (CVP) and pulmonary artery occlusion pressure (PAOP), often fail as meaningful tools for measuring the patient's hemodynamic state as they do not take into consideration the changes in other systemic interactions that can alter quickly. Indeed, studies in recent years have confirmed that such static measurements have little correlation with fluid responsiveness and are poor clinical indicators.

In many patients, a rapid fluid bolus is a reasonable diagnostic and potentially therapeutic option but, in others (e.g., acute respiratory distress syndrome), it has the potential to cause harm and may delay institution of appropriate therapy. An ideal system would be one in which it is possible to determine if a patient will be fluid-responsive before the fluid is given. The poor predictive value of static measurements and clinical examination has, therefore, led to the investigation of dynamic measurements of fluid responsiveness. In contrast to static measurements, dynamic indices rely mostly on the changing physiology of heart/lung interactions (e.g., measuring cyclic changes in cardiac filling status that are caused by mechanical ventilation) to determine whether a patient is fluid-responsive and will thereby benefit from therapeutic interventions. Indeed, there is growing evidence that dynamic markers (e.g., pulse pressure variation (PPV), systolic pressure variation, aortic blood flow velocity, and superior vena cava collapsibility) more accurately predict fluid responsiveness, than the static measurements traditionally used. Dynamic indices provide for a higher degree of accuracy in fluid responsiveness determinations with significantly reduced invasiveness.

Preload of the heart is defined as the wall stress at the end of diastole, i.e., left ventricular end-diastolic volume (LVEDV). Direct measurement of wall stress in vivo is difficult if not impossible within an emergency medicine department, surgical theater, and/or intensive care environment. Although end diastolic volumes or pressures have been used as proxies of wall stress, both have significant limitations. Perhaps most importantly, an accurate measure of preload at a point in time does not necessarily reflect fluid-responsiveness. An understanding of the Frank-Starling curve (an example of which is shown in FIG. 1) is fundamental to understanding the concept of fluid-responsiveness. The slope of the relationship between ventricular preload and stroke volume (SV) depends on ventricular contractility. As contractility increases, the Frank-Starling curve shifts upward and to the left and increases its slope. Decreasing contractility has the opposite effect. Increasing ventricular preload serves to augment ventricular output predominantly on the steep portion of the curve. As seen in FIG. 1, augmenting ventricular preload on the flat portion of the curve produces minimal increases in stroke volume. In normal physiologic conditions, both ventricles operate on the ascending portion of the Frank-Starling curve. This mechanism provides a functional reserve to the heart in situations of acute stress. In healthy patients, an increase in preload (with volume challenge) results in a significant increase in stroke volume. Furthermore, as a result of altered left ventricular compliance and function, the position of an acutely ill patient on their Frank-Starling curve cannot be predicted from their preload (LVEDV) alone. In critically ill patients it is therefore important not only to determine the patients' preload (LVEDV) but their fluid responsiveness, i.e., to whether the patient will increase their stroke volume or cardiac output with fluid loading. Therefore, even a precise measurement of left ventricular preload does not determine if that left ventricle is fluid-responsive (i.e., if it will increase cardiac output in response to increased volume). Additionally, the relationship between preload and stroke volume is curvilinear rather than linear as can be seen in FIG. 1.

Static Indices of Intravascular Volume

As a static measure of fluid-responsiveness, central venous pressure is frequently used to guide fluid management with reports indicating that over 90% of European intensivists/anesthesiologists used CVP to guide fluid management. The basis for using CVP to guide fluid management comes from the dogma that CVP reflects intravascular volume; specifically, it is widely believed that patients with a low CVP are volume depleted while patients with a high CVP are volume overloaded. A change in CVP following a fluid challenge is thereby used to guide subsequent fluid management decisions. CVP describes the pressure of blood in the thoracic vena cava near the right atrium of the heart. CVP is a good approximation of right atrial pressure, which is a major determinant of right ventricular filling. It has therefore been assumed that CVP is a good indicator of right ventricular preload. Furthermore, as right ventricular stroke volume determines left ventricular filling, the CVP is assumed to be an indirect measure of left ventricular preload. However, because of the changes in venous tone, intrathoracic pressures (positive end expiratory pressure, etc.), left and right ventricular compliance, and geometry that occurs in critically ill patients, it has been found that there is actually a poor relationship between CVP and right ventricular end-diastolic volume. Furthermore, the right ventricular end-diastolic volume may not accurately reflect the patient's position on the Frank-Starling curve and, therefore, their preload reserve.

Historically, medical practice for the measurement of hemodynamic blood flow parameters has been based on the use of a pulmonary artery catheter. This device is highly invasive and requires a catheter to be introduced through a large vein such as the jugular, subclavian, or femoral vein. The catheter is threaded through the right atrium and ventricle of the heart and into the pulmonary artery. The standard pulmonary artery catheter (also known as a "Swan-Ganz" catheter) has two lumens (tubes) and is equipped with an inflatable balloon at the tip, which facilitates its placement into the pulmonary artery through the flow of blood. The balloon, when inflated, causes the catheter to "wedge" in a small pulmonary blood vessel. So wedged, the catheter can provide a measurement of the blood pressure in the left atrium of the heart, termed Left Ventricular End Diastolic Pressure or LVEDP. Modern catheters have multiple lumens (multiple tubes) and have openings along the length to allow administration of inotropes and other drugs directly into the right atrium of the heart. The addition of a small thermistor temperature probe about 3 centimeters behind the tip allows the measurement of blood flow following calibration by means of the injection of a known volume and known temperature of cold fluid. As this cooler fluid passes the thermistor, a brief drop in the blood temperature is recorded. The resulting information can be used to compute and plot a thermodilution curve. If details about the patient's body mass index, core temperature, systolic, diastolic, central venous pressure, and pulmonary artery pressure are known/estimated and thereafter inputted into a diagnostic system connected to the Swan-Ganz catheter, a blood flow and pressure map can be calculated. The procedure is not without risk, and complications can be life threatening. It can lead to arrhythmias, rupture of the pulmonary artery, thrombosis, infection, pneumothorax, bleeding, and other life-threatening complications. Indeed, it was not long after the introduction of the pulmonary artery catheter that studies began to appear demonstrating that PAOP was a poor reflection of preload and more recent studies have demonstrated that pulmonary artery occlusion pressure (PAOP) is a poor predictor of preload and volume responsiveness. PAOP suffers many of the limitations of CVP: (i) PAOP is a measure of left ventricular end-diastolic pressure and not LVEDV or LV preload; (ii) use of PAOP to measure left ventricular preload assumes a direct relationship between the left ventricular end-diastolic pressure and LVEDV while the Frank-Starling principle shows that the pressure-volume curve describing left ventricular compliance is curvilinear; and (iii) alterations in left ventricular compliance shift the pressure-volume curve, for example.

Transesophageal echocardiography has also been used to assess left ventricular dimensions in patients undergoing mechanical ventilation. The left ventricular end-diastolic area (LVEDA) has been shown to correlate with the intrathoracic blood volume (ITBV) and global end-diastolic volume (GEDV), as well as with LVEDV as measured by scintography. For example, an end-diastolic diameter of <25 mm and a LVEDA of <55 cm2 have been used to diagnose hypovolemia. While a number of studies have found the LVEDA to be a good predictor of fluid responsiveness, other studies have failed to replicate such findings. A major limitation of echocardiography is that it provides a snapshot of ventricular function at a single period in time. Recently, a disposable transesophageal echocardiography probe that allows continuous monitoring (a more dynamic measurement) of LV function has been developed (ClariTEE™, ImaCor, Uniondale, N.Y., USA). Such technology allows monitoring of LV volumes and function over time, allowing the clinician to determine the response to various therapeutic interventions.

Dynamic Indices of Intravascular Volume

Dynamic indices, such as pulse pressure variation (PPV) and stroke volume variation (SVV), have traditionally applied a controlled and reversible preload variation and thereafter measured the hemodynamic response. This can be done by observing the cardiovascular response to positive pressure ventilation, or to reversible preload-increasing maneuvers, such as passive leg raising. One such prior art dynamic indices is a measurement of stroke volume variation which examines the differences between the stroke volume during the inspiratory and expiratory phases of ventilation and requires a means to directly or indirectly assess stroke volume. Stroke volume variation processes have traditionally required invasive monitoring such as aortic flow probes. Extravascular assessments of stroke volume have recently become available, however, the PiCCO™ system (Pulsion Medical Systems, Munich, Germany), the LiDCO™ system (LiDCO Group PLC, London, England), and FloTrac™ sensor system (Edwards Lifesciences, Irvine, Calif.) all have monitors that use pulse contour analysis through proprietary formulas that measure cardiac output and stroke volume variation using intravascular arterial pressure waveform analysis.

The principles underlying both PPV and SVV are based on the concept that intermittent positive pressure ventilation induces cyclic changes in the loading conditions of the left (LV) and right (RV) ventricles. Mechanical insufflation decreases preload and increases afterload of the RV. The RV preload reduction is due to the decrease in the venous return pressure gradient that is related in the inspiratory increase in pleural pressure. The increase in RV afterload is related to the inspiratory increase in transpulmonary pressure. The reduction in RV preload and increase in RV afterload both lead to a decrease in RV stroke volume, which is at a minimum at the end of the inspiratory period. The inspiratory reduction in RV ejection leads to a decrease in LV filling after a phase lag of two or three heart beats because of the long blood pulmonary transit time. Thus, the LV preload reduction may induce a decrease in LV stroke volume, which is at its minimum during the expiratory period. The cyclic changes in RV and LV stroke volume are greater when the ventricles operate on the steep rather than the flat portion of the Frank-Starling curve (see FIG. 1). Therefore, the magnitude of the respiratory changes in LV stroke volume is an indicator of biventricular preload dependence. It should be noted that arrhythmias and spontaneous breathing activity may lead to misinterpretations of the respiratory variations in PPV and SVV.

Monitoring of arterial blood pressure measured invasively through an arterial cannula placed in an artery, such as the radial, femoral, dorsalis pedis, or brachial artery, are used with respect to PPV monitoring. The arterial cannula is connected to a sterile, fluid-filled system, which is attached to an electronic pressure transducer. Pressure is constantly monitored beat-by-beat, and a waveform (a graph of pressure against time) can be displayed. Vascular pressure parameters, such as systolic, diastolic, and mean arterial pressure, are derived and displayed simultaneously for pulsatile waveforms. Such devices utilize pulse contour or pulse pressure wave analysis where the area under the systolic pressure wave curve is integrated, or wave characteristics are analyzed, and, when calibrated against either dye dilution or thermodilution, provide estimates of blood flow volume.

Cannulation for invasive vascular pressure monitoring is, however, associated with complications such as extravasation, thrombosis, and infection among other life threatening conditions. Patients with invasive arterial monitoring require very close supervision, as there is a danger of severe bleeding if the arterial line becomes disconnected. Peripheral vascular pressure monitoring devices are also known to be problematic in monitoring rapid changes in patients who are hemodynamically unstable. As such, these devices may and do lead to erroneous cardiac output measurements during the administration of vasoactive drugs, during loss of circulating volume, e.g., hemorrhage, insufflation of the abdomen for laparoscopic surgery, pathophysiological diseases resulting in abnormal arterial pressure waves, and positional changes during surgery. As but one example, drugs which create vasoconstriction result in an increase in systemic resistance and thus an increase in pressure which is interpreted as an increase in flow, whereas blood flow typically decreases as systemic resistance increases as the heart is acting to pump against increased resistance. Conversely, drugs which have a vasodilation effect result in a decrease in resistance to blood flow and typically blood pressure falls which is interpreted as a reduction in flow, whereas blood flow typically increases as systemic resistance decreases as the heart is acting to pump against a reduced resistance. Calibration is essential for absolute value accuracy and, in operating room conditions such calibration is complex to perform, is time consuming, needs to be repeated frequently, introduces chemical agents which may be toxic, and may be of limited accuracy in the presence of other drugs administered during patient treatment. As with extravascular ultrasound technologies (discussed further below), arterial blood pressure monitoring also requires the presence of a trained and experienced operator.

It has been found that superior vena cava (SVC) diameter is affected by the large fluctuations in intrathoracic pressure caused by positive pressure variation. A recent study by Vieillard-Baron et al., for example, noted a clustering of baseline SVC collapsibility between responders (with SVC collapse of 60% or more) and nonresponders (in whom SVC varied by 30% or less). "Superior vena cava collapsibility as a gauge of volume status in ventilated septic patients," Intensive Care Med 2004; 30:1734-39, the entire contents of which are hereby incorporated by reference in their entirety. This finding results in a specificity of 100% and a sensitivity of 90% for predicting a significant increase in cardiac output when the SVC collapsibility exceeds 36%. A disadvantage in monitoring SVC diameter variation as a dynamic indices of fluid responsiveness is that it requires transesophageal echocardiography which has all of the same disadvantages and limitations of other types of extravascular ultrasound—sensitivity to movement, user training and maintenance, and oftentimes difficult to visualize anatomical structures.

Extravascular Doppler measurements of variations of stroke volume have been used as an ultrasound technique for assessing dynamic indices of volume responsiveness. Fluctuations in stroke volume associated with ventilator cycling are greater in the hypovolemic patient than in the completely resuscitated patient. See, e.g., Feissel M. et al., "Respiratory changes in aortic blood velocity as an indicator of fluid responsiveness in ventilated patients with septic shock," Chest 2001; 119:867-73, the entire contents of which are hereby incorporated by reference in their entirety. The extravascular measurement of stroke volume by use of ultrasound and the Doppler principle relies upon the use of a probe containing piezoelectric crystals that are caused to emit either continuous wave or pulse wave ultrasound extravascularly into an adjacent arterial blood vessel. The probe may be located either in the esophagus, trachea, or is placed on the body surface in a position where an artery can be monitored. The velocity of the blood flow is calculated using the Doppler equation:

$$v = (c)(fD)/2(fT)\cos\Theta$$

where v is the velocity of the red blood cells, c is the speed of the ultrasound waves through body tissues, fD is the Doppler frequency shift, fT is the transmitted frequency of the ultrasound and Cos Θ is the cosine of the angle of insonation between the sound beam axis and the direction of blood flow. Such extravascular flow based measurements are, however, difficult to perform and require the presence of an operator that is capable of maintaining properly placement, alignment, and calibration of the ultrasound probe. The ultrasound beam is directional and is sensitive to movement, which requires the operator to check the beam's focus and thus the device cannot be considered to be providing continuous monitoring without operator attendance.

Acute Pulmonary Hypertension

Many complex medical disorders managed in intensive care units (ICU) are associated with an elevation of pulmonary arterial pressure (PAP). In some circumstances, serious and prolonged elevation of PAP progresses to severe acute pulmonary hypertension, leading to life threatening complications including, but not limited to, refractory systemic arterial hypotension, severe hypoxemia, right ventricular (RV) dysfunction and failure, and ultimately resulting in cardiogenic and/or obstructive shock and death. Clinical presentation, physical exam, electrocardiogram, ultrasound, and chest radiography can suggest pulmonary circulation abnormality. However, those data are not either specific enough or continuous to be useful in early diagnoses of acute pulmonary hypertension in intensive care units, nor for determining whether signs of acute pulmonary hypertension are hemodynamically significant. The use of Pulmonary Artery Catheter (PAC) capable of PAP monitoring has been significantly reduced due to its invasiveness and related safety concerns. Pulmonary hypertension is usually recognized when the patient develops obvious signs of progressive right ventricular failure, and during hemodynamic monitoring by echocardiogram or a pulmonary artery catheterization. Unfortunately, in most cases acute pulmonary hypertension remains under diagnosed or undiagnosed and treatment begins only after serious complications have developed. See, for example, Tsapenko et al., "Arterial pulmonary hypertension in noncardiac intensive care unit," Vascular Health and Risk Management 2008:4(5) 1043-1060, the entire contents of which are hereby incorporated by reference in their entirety.

Clinically significant onset of acute pulmonary hypertension causes the right ventricle of the heart to start to dilate. Higher pressure in the pulmonary artery (behind the right heart) may overload the right ventricle, causing the right ventricle to dilate or even fail. Even subtle dilation of the right ventricle may cause tricuspid valve insufficiency, that is, dysfunction of the valve between the right ventricle and the right atrium. The insufficiency of the tricuspid valve may cause backward leakage during right ventricle systole (that is, contraction). The backward leakage is known as Tricuspid Regurgitation (TR). The stronger the leak means the stronger the dilation of the right ventricle and the higher the level of right heart dysfunction caused by acute pulmonary hypertension onset. Current systems may monitor TR at the tricuspid valve using non-invasive TTE or TEE probes, producing data interpreted by sono specialists.

Given the limitations and complications of using current hemodynamic monitoring devices and methodologies, there is a need in the art for an improved method and apparatus for minimally invasive monitoring of the fluid-responsiveness of a patient continuously and in real time using dynamic indices. The presently disclosed and/or claimed inventive concept(s) disclose a method and apparatus that combines measurement of intravascular blood flow velocities simultaneously with respiratory cycle data to provide monitoring of a patient's fluid-responsive state and/or level of right ventricle dysfunction and/or acute pulmonary hypertension in a minimally invasive and operator independent process, thereby overcoming one or more of the aforementioned drawbacks found in the prior art apparatuses and techniques.

BRIEF DESCRIPTION OF THE SEVERAL VIEWS OF THE DRAWINGS

Certain embodiments of the present inventive concepts will hereafter be described with reference to the accompanying drawings, wherein like reference numerals denote like elements, and.

BRIEF DESCRIPTION

Figure 1:
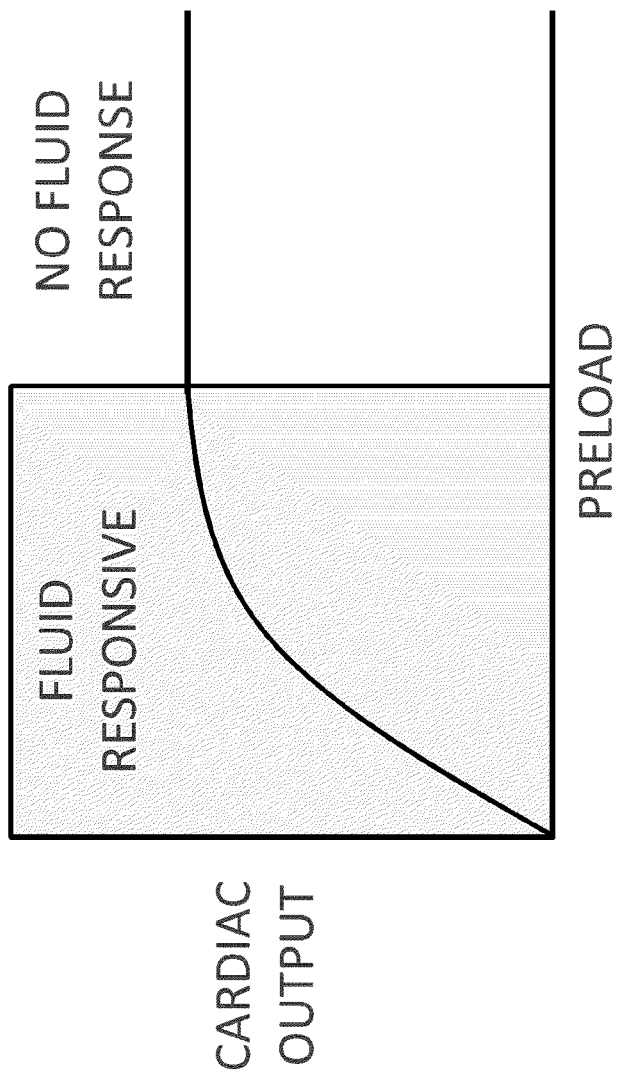
FIG. 1 depicts an exemplary Frank-Starling curve.

Consistent with one aspect of the present disclosure, a hemodynamic monitoring device may include a first sensor configured to measure a velocity of blood flow in an adjacently-located portion of a superior vena cava of a mammalian patient using ultrasound waves; a second sensor configured to measure respiratory cycle data of the mammalian patient; an input for receiving the measured velocity of blood flow and the measured respiratory cycle data; and a computer configured to process the measured velocity of blood flow and the measured respiratory cycle data to provide hemodynamic parameters corresponding to the mammalian patient.

Consistent with one aspect of the present disclosure, a hemodynamic monitoring device may comprise one or more processors executing logic to cause the hemodynamic monitoring device to receive one or more first electrical signals indicative of a fluid flow rate within an interior portion of a venous structure of a mammalian patient; receive one or more second electrical signals indicative of a respiratory cycle of the mammalian patient; analyze data indicative of the one or more first and second electrical signals to determine a fluid responsive state of the mammalian patient; and output at least one of visual indicia and audio communications representing the fluid responsive state of the mammalian patient to a user.

Consistent with one aspect of the present disclosure, a system for assessing hemodynamic parameters in a venous structure of a mammalian patient may comprise a catheter assembly having a distal end, a proximal end, and at least one lumen extending therebetween, the distal end of the catheter assembly capable of being advanced into an interior portion of the venous structure, wherein the distal end of the catheter assembly further comprises a first sensor configured to measure a fluid flow rate in the interior portion of the venous structure using ultrasound waves; a second sensor configured to measure respiratory cycle data of the mammalian patient; and a control unit configured to (i) cause the first sensor to emit an ultrasound wave and sense a response to the ultrasound wave, (ii) determine a flow rate of fluid passing through the venous structure using the sensed response to the ultrasound wave, and (iii) communicate to a user at least one of visual indicia and audio communications representing the fluid flow rate through the venous structure and the respiratory cycle data.

Consistent with one aspect of the present disclosure, a system for assessing hemodynamic parameters in a venous structure of a mammalian patient may comprise an elongate member deliverable to a venous structure of the mammalian patient such that a distal end of the elongate member penetrates the venous structure and is thereafter positioned within an interior portion of the venous structure, the distal end of the elongate member including a Doppler ultrasound sensor; a second sensor configured to measure respiratory cycle data of the mammalian patient; and a control unit configured to (i) cause the Doppler ultrasound sensor to emit an ultrasound wave, (ii) cause the Doppler ultrasound sensor to sense a response of the emitted ultrasound wave, (iii) determine a fluid flow rate through the venous structure and a respiratory cycle waveform of the mammalian patient, and (iv) communicate to a user at least one of visual indicia and audio communications representing the fluid flow rate through the venous structure and the respiratory cycle waveform of the mammalian patient.

Consistent with one aspect of the present disclosure, a method for assessing hemodynamic parameters in a venous structure of a mammalian patient may comprise the steps of receiving by a control unit one or more velocity input electrical signals, wherein the one or more input electrical signals are indicative of a velocity of fluid flow through the venous structure during a predetermined period of time; receiving by the control unit one or more respiratory input electrical signals, wherein the one or more respiratory electrical signals are indicative of a respiratory cycle waveform of a mammalian patient during the predetermined period of time, the respiratory cycle waveform comprising an inspiration time period and an expiration time period; analyzing by the control unit the one or more velocity input electrical signals and the one or more respiratory input electrical signals to determine changes in the velocity of fluid flow during the inspiration time period; and outputting by the control unit at least one output electrical signal responsive to the one or more velocity input electrical signals and the one or more respiratory input electrical signals to indicate at least one hemodynamic parameter of the mammalian patient.

Consistent with one aspect of the present disclosure, a method of assessing hemodynamic parameters in a venous structure of a mammalian patient may comprise the steps of inserting a distal end of a catheter through a tissue of the mammalian patient such that the distal end of the catheter is substantially adjacent an interior portion of the venous structure and a proximal end of the catheter is outside the mammalian patient and connected to a control unit, wherein the distal end of the catheter contains a Doppler ultrasound sensor; placing a respiratory sensor configured to measure respiratory cycle data on the mammalian patient; and activating a control unit configured to: (i) cause the Doppler ultrasound sensor to emit an ultrasound wave and sense a response to the ultrasound wave, (ii) determine a flow rate of fluid passing through the venous structure using the sensed response to the ultrasound wave, and (iii) communicate to a user at least one of visual indicia and audio communications representing the fluid flow rate through the venous structure and the respiratory cycle data.

Consistent with one aspect of the present disclosure, a hemodynamic monitoring device may comprise one or more processors executing logic to cause the hemodynamic monitoring device to receive one or more first electrical signals indicative of a fluid flow rate within an interior portion of a venous structure of a mammalian patient; receive one or more second electrical signals indicative of a respiratory cycle of the mammalian patient; analyze the one or more first and second electrical signals to determine a right ventricle dysfunctional state of the mammalian patient; and output at least one of visual indicia and audio communications representing the right ventricle dysfunctional state of the mammalian patient to a user.

Consistent with one aspect of the present disclosure, a system for assessing hemodynamic parameters in a venous structure of a mammalian patient may comprise a catheter assembly having a distal end, a proximal end, and at least one lumen extending therebetween, the distal end of the catheter assembly capable of being advanced into an interior portion of the venous structure, wherein the distal end of the catheter assembly further comprises a first sensor configured to measure a fluid flow rate in the interior portion of the venous structure using ultrasound waves; a second sensor configured to measure respiratory cycle data of the mammalian patient; and a control unit configured to (i) cause the first sensor to emit an ultrasound wave and sense a response to the ultrasound wave, (ii) determine a flow rate of fluid passing through the venous structure using the sensed response to the ultrasound wave, and (iii) communicate to a user at least one of visual indicia and audio communications representing the fluid flow rate through the venous structure and the respiratory cycle data.

Consistent with one aspect of the present disclosure, a system for assessing hemodynamic parameters in a venous structure of a mammalian patient may comprise an elongate member deliverable to a venous structure of the mammalian patient such that a distal end of the elongate member penetrates the venous structure and is thereafter positioned within an interior portion of the venous structure, the distal end of the elongate member including a Doppler ultrasound sensor; a second sensor configured to measure respiratory cycle data of the mammalian patient; and a control unit configured to (i) cause the Doppler ultrasound sensor to emit an ultrasound wave, (ii) cause the Doppler ultrasound sensor to sense a response of the emitted ultrasound wave, (iii) determine a fluid flow rate through the venous structure and a respiratory cycle waveform of the mammalian patient, and (iv) communicate to a user at least one of visual indicia and audio communications representing the fluid flow rate through the venous structure and the respiratory cycle waveform of the mammalian patient.

Consistent with one aspect of the present disclosure, a method for assessing hemodynamic parameters in a venous structure of a mammalian patient may comprise the steps of receiving by a control unit one or more velocity input electrical signals, wherein the one or more input electrical signals are indicative of a velocity of fluid flow through the venous structure during a predetermined period of time; receiving by the control unit one or more respiratory input electrical signals, wherein the one or more respiratory electrical signals are indicative of a respiratory cycle waveform of a mammalian patient during the predetermined period of time, the respiratory cycle waveform comprising an inspiration time period and an expiration time period; analyzing by the control unit the one or more velocity input electrical signals and the one or more respiratory input electrical signals to determine changes in the velocity of fluid flow during the inspiration time period; and outputting by the control unit at least one output electrical signal responsive to the one or more velocity input electrical signals and the one or more respiratory input electrical signals to indicate at least one hemodynamic parameter of the mammalian patient.

Consistent with one aspect of the present disclosure, a method of assessing hemodynamic parameters in a venous structure of a mammalian patient may comprise the steps of inserting a distal end of a catheter through a tissue of the mammalian patient such that the distal end of the catheter is substantially adjacent an interior portion of the venous structure and a proximal end of the catheter is outside the mammalian patient and connected to a control unit, wherein the distal end of the catheter contains a Doppler ultrasound sensor; placing a respiratory sensor configured to measure respiratory cycle data on the mammalian patient; and activating a control unit configured to: (i) cause the Doppler ultrasound sensor to emit an ultrasound wave and sense a response to the ultrasound wave, (ii) determine a flow rate of fluid passing through the venous structure using the sensed response to the ultrasound wave, and (iii) communicate to a user at least one of visual indicia and audio communications representing the fluid flow rate through the venous structure and the respiratory cycle data.

Consistent with one aspect of the present disclosure, one or more velocity input electrical signals may be produced by an intravascular Doppler ultrasound probe sensor and/or a Laser Doppler Velocimetry sensor and/or an ultrasound M-Mode sensor.

Consistent with one aspect of the present disclosure, a sensor may also measure the diameter of a vein in substantially the same location where the blood velocity is monitored.

DETAILED DESCRIPTION

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description or illustrated in the drawings. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those of skill in the art that variations may be applied to the articles and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" in may mean "one," but it is also consistent with the meaning of "one or more," "at least one," and "one or more than one." The use of the term "or" is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the terms "about" or "approximately" are utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example. Further, use of the term "plurality" is meant to convey "more than one" unless expressly stated to the contrary. When ranges are listed, the ranges will be understood to encompass any and all values in the range, including the beginning and ending values.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used in the instant disclosure the terms "provide," "providing" and variations thereof as used herein comprise displaying, or providing for display, a screen either by one or more monitors (hereinafter referred to as a monitor) via a computer located locally with respect to the monitor or by a host computer located remotely from the monitor. The computer or host computer may interface with a computer network and/or allow the one or more computer to obtain information from a host computer by sending and/or receiving digital and/or optical signals via a computer network interface (e.g., an Ethernet port, a TC/IP port, an optical port, a cable modem, and combinations thereof), for example.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The presently disclosed and/or claimed inventive concept(s) relates generally to a hemodynamic monitoring device and methods of making and using same. Broadly, the hemodynamic monitoring device is capable of collecting data from a mammalian patient (such as a human), transforming the collected data into information correlated with a fluid responsiveness and/or level of right ventricle dysfunction and/or acute pulmonary hypertension of the mammalian patient, and providing the information in a format capable of being perceived by a healthcare provider such as a doctor or a nurse. Such data is collected, transformed and provided on a continuing basis and in real-time (i.e., in a dynamic manner). In one embodiment, the data collected from the mammalian patient may include respiratory cycle data and at least one of a velocity of blood flow in the superior vena cava, central venous pressure, and combinations thereof. In one embodiment, the respiratory cycle data of the mammalian patient may be correlated with at least one of the velocity of blood flow in the superior vena cava, the central venous pressure, the diameter of the superior vena cava, and combinations thereof in order to provide information that is thereby calculated and correlated with the fluid responsive state and/or level of right ventricle dysfunction and/or acute pulmonary hypertension of the patient. The hemodynamic monitoring device includes sensors to minimally invasively measure the velocity of blood flow in the superior vena cava, central venous blood pressure, diameter of the superior vena cava, and/or the respiratory cycle data of the patient. In particular, changes in the superior vena cava diameter as well as changes in the velocities of blood flow in the superior vena cava and in the central venous pressure occurring throughout the respiratory cycle data are sensed by the sensors and provided to a patient device and a computer in a continuing and real-time manner. The computer transforms the data into information correlated with the fluid responsiveness and/or level of right ventricle dysfunction and/or acute pulmonary hypertension of the mammalian patient, and provides the information to a display in order to provide an observer of the data, e.g., a surgeon, nurse or anesthesiologist, with a dynamic indicator of the fluid responsive state and/or level of right ventricle dysfunction and/or acute pulmonary hypertension of the patient.

As will be explained, in one embodiment the hemodynamic monitoring device includes suitable hardware and software to obtain measurements of the respiratory cycle data of the patient and correlate this information with at least one of (1) velocity of blood flow in the patient's superior vena cava, (2) the patient's central venous blood pressure, (3) the diameter of the superior vena cava, and (4) combinations thereof. One aspect of the presently disclosed and/or claimed inventive concept(s) is to combine the beneficial attributes of blood flow within the superior vena cava, as measured by a Doppler ultrasound sensor and/or a Laser Doppler Velocimetry sensor and/or an ultrasound M-Mode sensor, with data representing the respiratory cycle of the patient as measured by an airway pressure transducer assembly, for example. Another aspect of the presently disclosed and/or claimed inventive concept(s) is to combine the beneficial attributes of central venous pressure within the superior vena cava, as measured by way of venous pressure sensor technologies, with data representing the respiratory cycle of the patient as measured by an airway pressure transducer assembly, for example. Yet another aspect of the presently disclosed and/or claimed inventive concept(s) is the combination of the beneficial attributes of central venous pressure and blood flow within the superior vena cava, as measured by way of Doppler ultrasound sensor, and/or Laser Doppler Velocimetry sensor, and venous pressure sensor technologies, with data representing the respiratory cycle of the patient as measured by an airway pressure transducer assembly, for example. The data collected by the Doppler ultrasound sensor, the airway pressure transducer assembly (for example), and the venous pressure sensor technologies may be provided to a patient interface unit in an analog format. In this instance, the patient interface unit may transform the data in the analog format into digital data which can be transferred to the computer by way of a data bus. For example, the patient interface unit may transform the analog data into a USB 2.0 format, or the like.

In a first embodiment, the hemodynamic monitoring device includes a first sensor configured to measure a velocity of blood flow in an adjacently located portion of the superior vena cava of a patient; a second sensor configured to measure respiratory cycle data of the patient; and the patient device for receiving the data indicative of measured velocity of blood flow and the measured respiratory cycle data. The hemodynamic monitoring device receives signals from each of the first and second sensors (which may be in digital and/or analog format) representing the measured velocity of blood flow and the measured respiratory cycle data and thereafter processes and transforms the measured velocity of blood flow and the measured respiratory cycle data to provide hemodynamic parameters corresponding to the mammalian patient.

Figure 2:
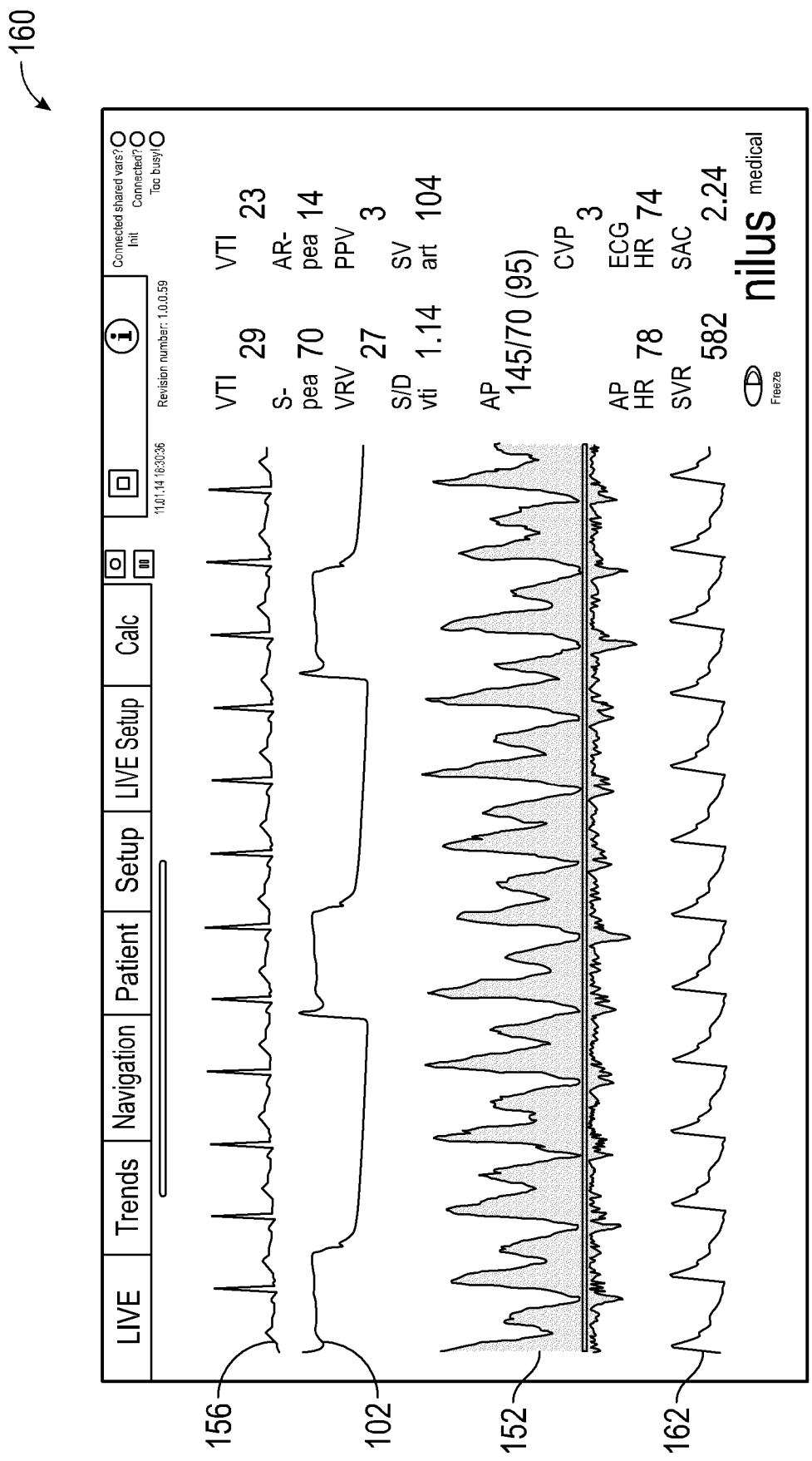
FIG. 2 depicts a screenshot of an exemplary display of waveforms in accordance with the present disclosure.

Velocity of blood flow measurements ("blood flow measurements") within the superior vena cava may be made by the first sensor simultaneously with measurements of the respiratory cycle data of the patient by the second sensor and then correlated and transformed into information for monitoring the patient's fluid responsive state and/or level of right ventricle dysfunction and/or acute pulmonary hypertension. The first sensor configured to measure velocity of blood flow measurements may include an intravascular Doppler probe placed within a central venous catheter of the mammalian patient. The intravascular Doppler probe may utilize a continuous wave or pulse wave ultrasound beam or laser beam for the measurement of blood flow in the superior vena cava to thereby generate analog and/or digital signals indicative of the measurements of the blood flow. In one embodiment, the signals obtained from the intravascular Doppler are interpreted to thereby provide an instant peak velocity of blood flow at one or more discrete measurement times. In a specific embodiment, the intravascular Doppler probe provides signals correlating to or representing a series of instant peak velocities over a predefined period of time. For example, the intravascular Doppler probe may provide signals correlating to or representing a series of instant peak velocities for 5, 10, 20, 30, 40, 50, 60 seconds and/or 1, 5, and/or 10 minutes—that is, the instant peak velocities may be obtained for any time period desired by the practitioner or clinician. The series of instant peak velocities obtained through the signals provided by the intravascular Doppler probe may provide, over time, a waveform representing the instant peak velocity of the blood flow as encountered by the patient over predefined period of time (as shown in FIG. 2).

The respiratory cycle data measurements are made by the second sensor. The second sensor may include a monitoring sensor placed adjacent to an appropriate anatomical structure wherein the monitoring sensor is capable of acquiring data indicative of respiratory cycle data of the patient. For example, the second sensor may include ECG sensors attached to the mammalian patient for acquiring the respiratory cycle data (in analog and/or digital format) utilizing impedance measurements. ECG data may include such data as Heart Rate (HR) (number of R-R wave intervals per minute), Heart Rhythm, Extrasystoles, and/or P-wave detection data. Alternatively, the second sensor may include an airway pressure transducer attached or operatively coupled with a ventilation assembly artificially ventilating the patient to acquire the respiratory cycle data (in analog and/or digital format).

Figure 3:
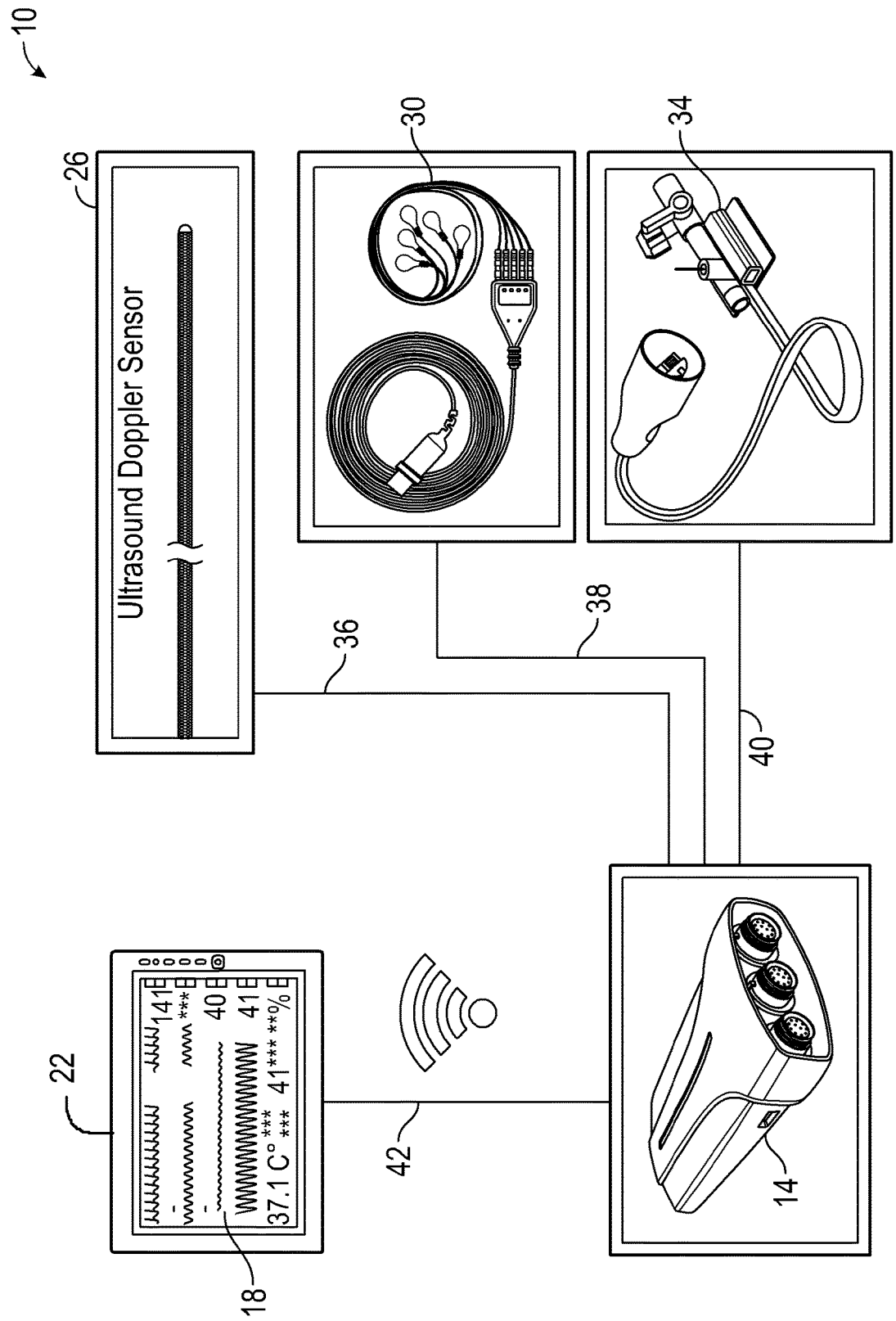
FIG. 3 is a perspective view of an exemplary hemodynamic monitoring device constructed in accordance with the present disclosure.

Referring now to the Figures and, in particular to FIG. 3, shown therein and designated by reference numeral 10 is a hemodynamic monitoring device constructed in accordance with the present disclosure. In one embodiment, the hemodynamic monitoring device 10 is provided with a patient interface unit 14, a display 18, a computer 22, a first sensor 26, a second sensor 30, and an optional third sensor 34. Additional sensors, as will be understood by one of ordinary skill in the art, can also be configured and used with the hemodynamic monitoring device 10, e.g., sensors for central venous pressure measurement, arterial pressure measurement, and airway pressure measurement. As will be discussed in more detail below, the patient interface unit 14, the display 18, the computer 22, the first sensor 26, the second sensor 30 and the optional third sensor 34 are all adapted and configured to communicate with one another utilizing any suitable technology such as cables and/or wireless communication systems.

In general, the first sensor 26, the second sensor 30 and the optional third sensor 34 collect multiple different types of data simultaneously from the mammalian patient and then provide the collected data to the patient interface unit 14 via signal paths 36, 38 and 40. As shown in FIG. 3, the signal paths 36, 38 and 40 may be cables which convey the data in electronic form. Normally, the data collected from the mammalian patient is in an analog format. In this instance, the patient interface unit 14 transforms the data from the analog format into a digital format suitable for use and interpretation by the computer 22. The patient interface unit 14 outputs the data, which is normally in the digital format, to the computer 22 via signal path 42. The signal path 42 may be a data bus, for example. The computer 22 receives the data, normally in the digital format, and correlates the various different types of data into information indicative of hemodynamic parameters corresponding to the mammalian patient, and then generates and provides output signals to a signal path 44 (shown in FIG. 4) connected to the display 18. The signal path 44, for example, can be a data bus or a video cable connecting the computer 22 to the display 18. In any event, the display 18 receives the output signals from the second path 44 and then generates and displays a screen of the hemodynamic parameters such that an observer such as a doctor, anesthesiologist or a nurse may observe the hemodynamic parameters and proceed accordingly based upon their own expertise.

Figure 4:
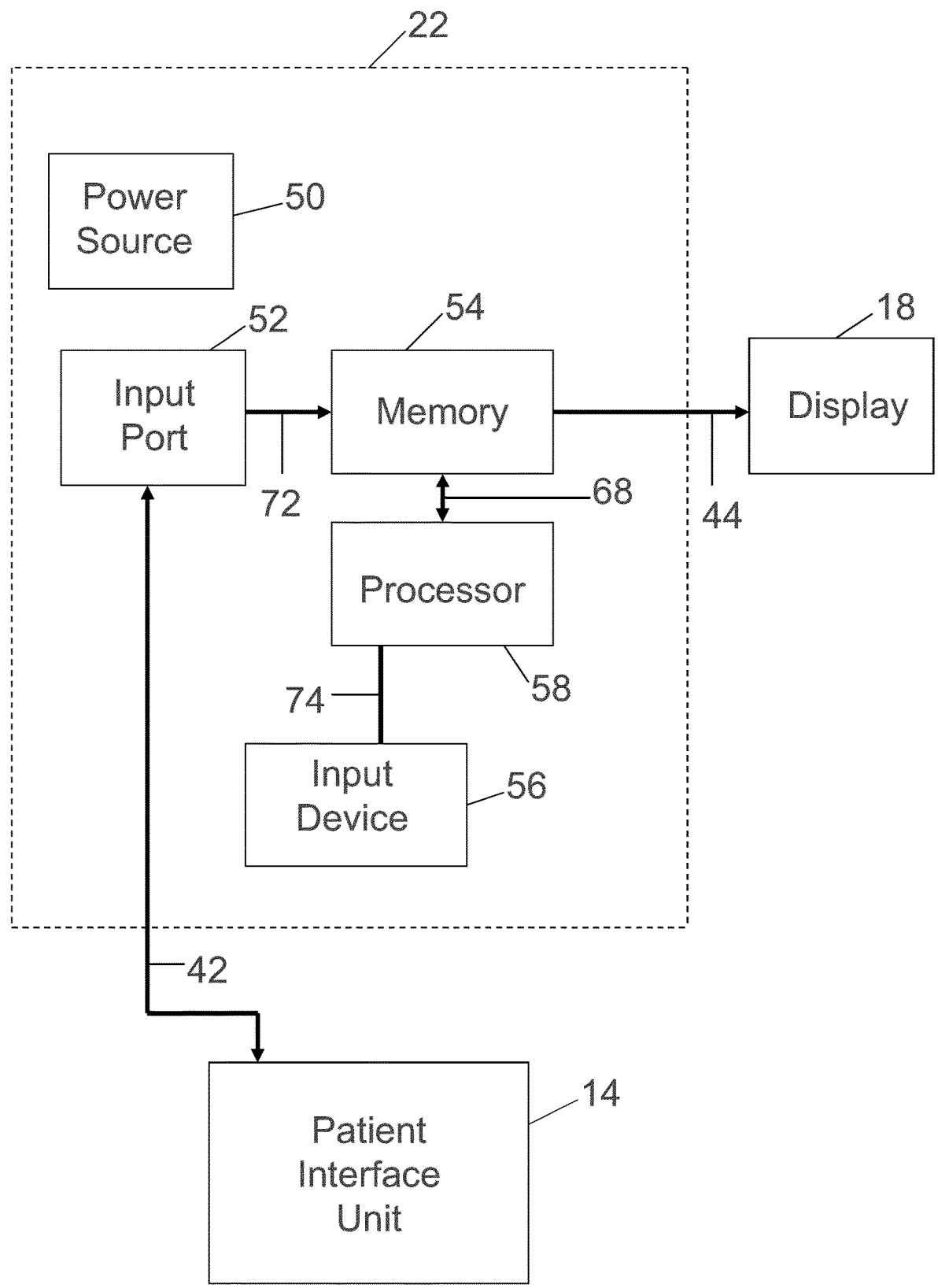
FIG. 4 is a block diagram of a computer, a display and a patient interface unit of the hemodynamic monitoring device depicted in FIG. 3.

Shown in FIG. 4 is a block diagram of the computer 22, which is connected to the patient interface unit 14 and the display 18 by way of the signal paths 42 and 44. In general, the computer 22 is provided with one or more power sources 50, one or more input ports 52, one or more memories 54, one or more input devices 56 and one more processors 58 all of which will be referred to hereinafter in the singular for purposes of clarity. The input port 52, the memory 54, the input device 56 and the processor 58 can be stand-alone, partially or completely network-based or cloud-based, and may be located in a single physical location or not necessarily located in a single physical location. For example, a portion of the memory 54 may be a cloud-based memory.

The processor 58 of the computer 22 is capable of executing processor executable code stored on the memory 54. The processor 58 can be implemented as a single processor 58 or multiple processors 58 working together to execute the logic described herein. Exemplary embodiments of the processor 58 include a digital signal processor (DSP), a central processing unit (CPU), a field programmable gate array (FPGA), a microprocessor, a multi-core processor, and combinations thereof. The processor 58 is capable of communicating with the memory 54 via a signal path 68 which can be implemented as a data bus or a network, for example. The processor 58 is capable of communicating with the input device 56 via a signal path 70 which may be a data bus or a network, for example. The processor 58 is further capable of interfacing and/or communicating with the patient interface unit 14 via the input port 52 and signal paths 72 and 42, such as by exchanging electronic, digital and/or optical signals via one or more physical or virtual ports using a network protocol such as TCP/IP, for example. The signal path 42 can also be implemented with a serial and/or parallel cable utilizing any suitable protocol. It is to be understood that in certain embodiments using more than one processor 58, the one or more processor 58 may be located remotely from one another, located in the same location, or comprising a unitary multi-core processor (not shown). The processor 58 is capable of reading and/or executing processor executable code and/or or creating, manipulating, altering, and storing computer data structures into the memory 54.

The memory 54 stores processor executable code for causing the processor 58 to implement the functions described herein. The memory 54 may be implemented as any conventional non-transitory memory, such as random access memory (RAM), a CD-ROM, a hard drive, a solid state drive, a flash drive, a memory card, a DVD-ROM, a floppy disk, an optical drive, a compact flash drive, holographic drives, and combinations thereof, for example. It is to be understood that the memory 54 can be located in the same physical location as the processor 58, the memory 54 may be located remotely from the processor 58 and may communicate with the processor 58 via a network. Additionally, when more than one memory 54 is used, the multiple memories 54 may be located in the same physical location as the processor 58, and one or more of the multiple memories 54 may be located in a remote physical location from the processor 58. The physical location(s) of the one or more memory 54 can be varied, and the memory 54 may be implemented as a "cloud memory", i.e., one or more memory which is partially or completely based on or accessed using a network.

The input device 56 transmits data to the processor 58 via a signal path 74 and can be implemented as a keyboard, a mouse, a touch-screen, a camera, a cellular phone, a tablet, a smart phone, a PDA, a microphone, a network adapter, a probe having a sensor therein, and combinations thereof, for example but not by way of limitation. The signal path 74 may include a cable, a data bus, a wireless link, a network and combinations thereof. Any device capable of functionally transmitting data to the processor 58 can be used as the input device 56. The input device 56 may be located in the same physical location as the processor 58 or may be remotely located and/or partially or completely network-based.

The display 18 transmits information from the processor 58 to an observer, such that the information can be perceived by the observer. For example, but not by way of limitation, the display 18 can be implemented as a computer monitor, a cell phone display, a tablet display, a website, a projector, a laptop monitor, and combinations thereof. In one embodiment, the computer 22 can be integrated with the display 18. For example, the computer 22 and the display 18 can be components of a tablet or laptop computer. The display 18 can be physically co-located with the processor 58, or can be located remotely from the processor 58, and may be partially or completely network based (e.g., a website). The display 18 communicates with the processor 58 via the signal path 44. As used herein, the term "user" is not limited to a human, and may comprise a human using a computer, a host system, a smartphone, a tablet, a computerized pen or writing device, and combinations thereof, for example but not by way of limitation.

In one embodiment, the display 18 is a touch screen display. In this embodiment, the touch screen display forms the input device 56 and the display 18. The touch screen display is preferably equipped with a graphical user interface (GUI) capable of communicating information to the user and receiving instructions from the user. The computer 22 may also include a housing containing computer hardware and software implementing the processor 58, the input port 52, and the memory 54 to control the first sensor 26, second sensor 30, and third sensor 34 via the patient interface unit 14, receive digitized signals and other information from the patient interface unit 14, and process the data, such as the Doppler data indicative of blood flow velocity in the superior vena cava, and the respiratory data, to correlate the blood flow velocity data with the respiratory data as discussed above.

In particular, the processor 58 correlates the data indicative of blood velocity waveform changes within central veins, such as the superior vena cava, against various phases of respiratory cycle to provide a set of to be monitored values indicative of the mammalian patient's fluid responsiveness status and/or level of right ventricle dysfunction and/or acute pulmonary hypertension. Various hemodynamic parameters such as venous flow, peak velocities, and S/D/VR and AR wave changes can be observed and monitored by the observer. Also absolute values of these parameters may be calculated and displayed to allow for calculation of indexes indicative of the patient's hemodynamic status and fluid responsiveness, which may be known as volume responsiveness, and/or calculation of indexes indicative of the patient's level of right ventricle dysfunction and/or acute pulmonary hypertension.

It should be understood that a central vein, such as the superior vena cava may be hard to collect data from with traditional Doppler probes used externally on the chest or through transesophageal access. However, the first sensor 26 may be implemented with an intravascular Doppler probe for monitoring of velocity of the blood flow within the central vein, such as the superior vena cava. The first sensor 26 may monitor antegrade and/or retrograde flow. The first sensor 26 can also be made capable of measuring the diameter of the central vein in substantially the same location where the blood velocity is monitored. For example, a simple m-mode ultrasound transducer may be placed near the Doppler probe. In one embodiment, miniature crystals may be built into the first sensor 26 in addition to a Doppler crystal. The miniature crystals are adapted to emit ultrasound waves in a direction of a wall and receive ultrasound reflections detecting distance of venous walls from the sensor 26. At least two such crystals emitting waves in opposite directions would provide information indicative of the diameter of the vein in the same location where the velocity is measured. The first sensor 26 could thereby continuously monitor changes in venous diameter.

The monitoring of fluid responsiveness provides the observer with independent, continuous, real time or near real time monitoring of central hemodynamics of the mammalian patient. Further, monitoring of fluid responsiveness in central veins avoids some limitations pertaining to other methods because the superior vena cava, for example, is not subject to single location change in vascular tonus as in the case of peripheral arteries. Cardiovascular compensatory mechanisms are more obscure on a venous side. Some arrhythmias do not influence monitoring as in the case of arterial pressure waveforms.

The first sensor 26 may be positioned in front of the right atrium in the superior vena cava such that the first sensor may detect a backwards leak from tricuspid regurgitation (TR), such as that caused by dilation of the right ventricle in acute pulmonary hypertension. Typically, blood flow in the superior vena cava is dominantly antegrade by nature with small retrograde pulses caused physiologically by contraction of the right atrium. However, when acute pulmonary hypertension develops with consequent tricuspid regurgitation, the antegrade flow may decrease and the retrograde flow may increase during systole, because of the backward leakage of the tricuspid valve. Retrograde flow in diastole may also increase as a result of the blood congestion in front of the right heart, either due to right heart failure or simply due to increased preload. In ventilated patients the effect of the tricuspid regurgitation might be more pronounced during the inspiration phase than during the expiration phase, as inspiration increases pulmonary hypertension.

The first sensor 26 implemented as an intravascular Doppler probe allows for continuous dynamic assessment of right heart dysfunction through monitoring the flow patterns. These data may be presented as antegrade systolic waveforms, retrograde systolic waveforms, antegrade diastolic waveforms, and/or retrograde diastolic waveforms on a pulsed Doppler velocity flow chart, for example, as discussed in conjunction with FIGS. 11 and 12.

The primary functions of the software stored on the memory 54 of the computer 22 may be receiving user commands via the input device 56, activate collection of the data discussed above utilizing the first sensor 26, the second sensor 30 and the other sensors 34, processing the data received from the first sensor 26, the second sensor 30 and the other sensors 34 into the information indicative of the patient's hemodynamic status, fluid responsiveness and/or level of right ventricle dysfunction and/or acute pulmonary hypertension, according to defined algorithms stored on the memory 54, displaying received parameters and processed data, and monitoring system status and reporting fault conditions.

The patient interface unit 14 is connected to the computer 22 via the signal path 42 which may be a parallel or serial cable and contains the electrical connections to all electrodes, signal conditioning circuitry, stimulator drive if used by the first sensor 26, the second sensor 30 and/or the other sensors 34, and a digital communications interface to the computer 22. In use, the computer 22 may be situated outside but close to the surgical field (such as on a cart adjacent the operating table) such that the display 18 is directed towards the surgeon for easy visualization. The patient interface unit 14 may be located on the patient's bed, or may be affixed to the end of the operating table at mid-leg level using a bedrail clamp, or may be affixed to a bedside pole. The position selected should be such that the leads can reach their farthest desired location without tension during the surgical procedure.

Figure 5:
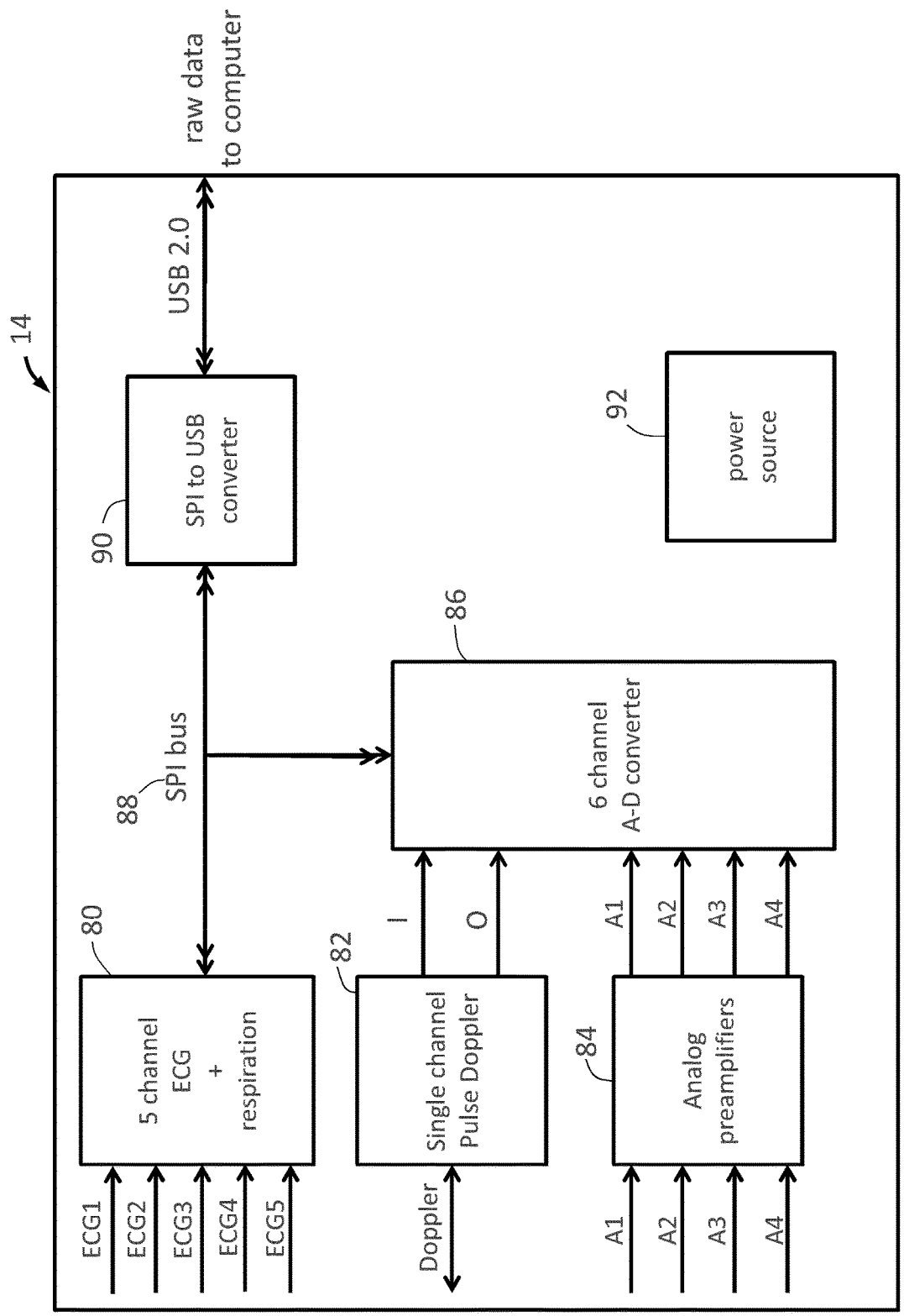
FIG. 5 is an exemplary block diagram of the patient interface unit depicted in FIG. 3.

Referring now to FIG. 5, shown therein is an exemplary block diagram of the patient interface unit 14. In general, the patient interface unit 14 is provided with one or more interface devices such as a first interface device 80, a second interface device 82, and a third interface device 84. In the example shown, the first interface device 80 is a five channel electrocardiograph and respiration device having a plurality of input ports for receiving up to five electrocardiograph signals from the second sensor 30. The first interface device 80 may use a dedicated chip having an ECG front-end with 5 channels ECG+respiration measurements. Airway Pressure may be acquired via pressure transducer connected to open vent of patient's airways (possible through use of the third interface device analog channels). Respiration may be based on impedance measurement to measure changes of thoracic volume based on electrode displacement. Respiration data may be acquired through bioimpedance measurement of chest wall movement during inspiration and expiration, or acquired by other methods. Measurement may be accomplished via ECG leads placed on the patient's chest, with one lead being active and a second lead being passive.

In one embodiment, the first interface device 80 may use Analog Devices chip ADAS 1000. This chip features ECG+respiration+leads-off detection and digital interface—SPI bus.

The second interface device 82 may be a single channel pulse Doppler device that transmits signals to the first sensor 26 to cause the first sensor 26 to emit radiofrequency signals and also receive reflections from the ultrasonic signals into transmit Doppler radar signals to the second interface device 82. Single channel pulse Doppler includes a switcher, a transmitter and a receiver of Doppler signal. The second interface device 82 may use a single crystal probe in which the crystal acts as an emitter and a receiver. In this example, the second interface device 82 includes a switcher for switching between the receiving and transmitting of signals. The transmitter sends pulses of RF (radiofrequency) signal to a probe of the first sensor 26 in order for the probe to act as a receiver for signals between pulses. For amplification of the RF signal and extraction of the Doppler signal from probe, the receiver may use a suitable integrated circuit, such as an analog devices chips—AD 8332 (dual channel ultra-low noise variable gain amplifier, dedicated for ultrasound systems) and AD 8333 (dual phase shifter and I-Q demodulator for ultrasound systems).

The third interface device 84 can include any suitable type of circuitry for causing the third sensor 34 to collect data from the mammalian patient. For example, when the third sensor 34 includes one or more pressure transducer, the information displayed to the user on touch screen display 18 may include, but is not necessarily limited to, alpha-numeric and/or graphical information regarding invasive pressure monitoring, such as arterial pressure, central venous pressure, and so on. Also airway pressure signal for respiration cycle monitoring may be channeled in through this device. In the example shown in FIG. 5, the third interface device 84 is a four channel analog preamplifier device having a plurality of input ports for receiving up to four signals from the third sensor 34.

The first, second, and third interface devices 80, 82, and 84 may transmit signals to an Analog-Digital (A-D) converter 86. The A-D converter 86 may be, for example, an A-D converter chip from Analog Devices—AD7656-1—which features a six channel A-D converter with maximum sample rate 250 kSPS (kilo-samples per second) and sixteen bit resolution. As shown in the example illustrated in FIG. 5, two channels of the A-D converter 86 may be used for processing of a raw Doppler signal from the second interface device—I and Q phase quadrature outputs raw signal which gives after processing forward and reverse components of blood flow signal and after another processing (complex Fourier transform) direct values of blood flow velocities. Another four channels of the A-D converter 86 may be used for optional analog inputs A1, A2, A3, and A4 from the third interface device 84.

The A-D converter 86 may have digital output to parallel or serial interface—SPI bus. For example, the digital signals from the A-D converter 86 may be sent over a Serial Peripheral Interface (SPI) bus 88, which is generally not suitable for direct interfacing to the computer 22. A SPI-to-USB converter 90 may be used between the A-D converter 86 and the computer 22, as well as between the first interface device 80 and the computer 22. The SPI-to-USB converter 90 may send digital signals over USB 2 (full speed) to the computer 22. Data transmission to the computer 22 may be wireless. The computer 22 may be equipped with a driver for interfacing with the SPI-to-USB converter 90 and transmitting data. The SPI-to-USB converter 90 may be equipped with a USB digital isolator for ensuring electric isolation between the patient interface unit 14 and the computer 22, thus ensuring patient safety.

The patient interface unit 14 may also be provided with a power source 92. Of course, it should be understood that the power source 92 may be internal to, or external to, the patient interface unit 14.

The computer 22 may execute software to process the data received from the patient interface unit 14 and store the data in memory 54 and/or display the data on the display 18. In one example, the computer 22 may scale the data, that is, convert the raw digital input to a representation with a desired physical unit. One example of scaled data is the conversion of Volts to mmHg. The computer 22 may add channel attributes to the scaled data, for example, calibration constants. The computer 22 may execute software to perform real-time calculations on the incoming data and then may display results on the display 18. The computer 22 may calculate data trends and display the data trends on the display 18. The data trends and calculation results may be stored in memory 54.

In one embodiment, the computer 22 receives from the first and second sensors 26, 30, through the patient interface unit 14, Doppler sensor input, Respiration input, and ECG input. The computer 22 may also receive from the first and/or second sensors 26, 30 superior vena cava diameter input. The computer 22 may receive from the third sensor(s) 34 Central Venous Pressure Input (CVP) and/or Arterial Pressure Input (AP). The computer 22 may display real-time waveforms of the inputs on the display 18 and/or may calculate additional data from the inputs. Calculations may include hemodynamic parameters such as Average Peak Velocity, Venous Return Variation (VRV) Index, Venous Return (VR), Preload, Stroke Volume, Cardiac Index, Stroke Index, Systemic Vascular Resistance, Systemic Arterial Compliance, and/or Central Venous Pressure, Central Venous Pressure Variation Index and Arterial Pressure (which may include Pulse Pressure Variation). For example, the computer 22 may calculate Average Peak Velocity (APV) during inspiration and/or expiration. APV may be calculated as an average value of all instant peak velocity samples within a defined calculation time frame. The computer 22 may also calculate Venous Return Variation (VRV) Index between inspiration and expiration phases of the respiratory cycle using, for example, the following algorithm (where AVPexp is AVP during expiration, and AVPinsp is AVP during inspiration):

$$VRV=(APVexp-AVPinsp)/Average(APVexp:APVinsp) \times 100$$

The computer 22 may also calculate Venous Return Variation (VRV) Index between inspiration and expiration phases of the respiratory cycle using, for example, the following algorithm (where APVmin is the beat with the smallest APV, and APVmax is APV with greatest APV out of every respiration cycle):

$$VRV=(APVmax-APVmin)/Average(APVmax:APVmin) \times 100$$

VRV index may be used as an indicator correlating with fluid responsiveness of the mammalian patient.

The computer 22 may output the monitored input hemodynamic data and calculated hemodynamic data in a format readable by the user on the display 18. The data may be displayed in real-time or as historical data. Data may be displayed in the form of charts and/or figures. Color may be used to illustrate the data in the charts and/or figures. In one embodiment, a user may zoom and pan within the displayed charts and figures.

Figure 6:
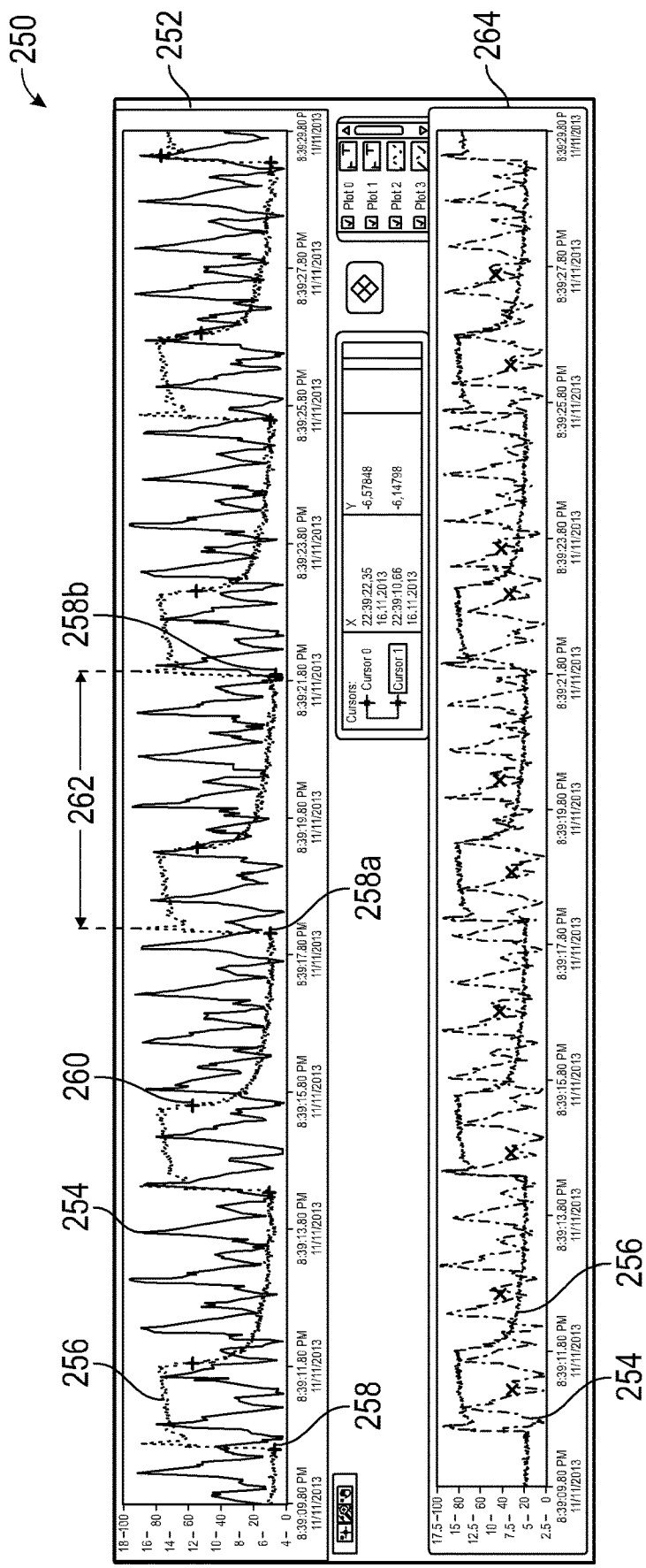
FIG. 6 depicts a screenshot of VRV Index data in accordance with the present disclosure.

In one example of displayed data, FIG. 6 depicts a screenshot 250 of data for a calculated VRV Index. A first chart 252 depicts a Doppler flow velocity envelope 254 and a respiration waveform 256. Cross "+" marks indicate the start of inspiration 258 and the start of expiration 260, with the period between a first inspiration start 258a and a next respiration start 258b being one respiration cycle 262. A second chart 264 depicts the Doppler flow velocity envelope 254 and the respiration waveform 256 with "x" marks indicating the mammalian patient's heart beats that have minimal and maximal average flow velocities. The minimal and maximal average flow velocities may be used to calculate the VRV Index for a respiration cycle 262 and/or for multiple respiration cycles 262. In one example, an average VRV Index may be displayed on the screen 18.

The computer 22 may calculate Venous Return (VR). One algorithm for VR may be as follows: VR=SVC VTI×SVC Cross section×1/Percentage of SVC Flow out of total VR. In this example, SVC VTI stands for Superior Vena Cava Velocity Time Integral, which may be measured from Instant Peak Velocity over a defined calculation time frame, where the computed value may be normalized to one minute. VTI may be an integral of a peak velocity waveform. SVC Cross section may be calculated from the patient's Body Mass Index Surface Area and height, or manually inputted. SVC Flow contribution to the total Venous Return is typically defined by the patient's age, or manually inputted. Heart Rate (HR) is defined as the number of heart beats per minute (number of RR intervals on ECG or number of AP amplitudes/minute). SV is defined as Cardiac Output (CO) divided by Heart Rate (HR), where VR in steady state equals Cardiac Output.

The computer 22 may calculate a preload surrogate. The preload surrogate may be derived from the Venous Return (VR) during inspiration. Venous Return per minute is equivalent to Cardiac Output (CO). Venous Return is driven by pressure gradient between peripheral veins and the right atrium of the heart. Stressed (hemodynamically active) volume of the blood in peripheral veins is the main driver of the preload and drives Peripheral Venous Pressure. Right Atrium Pressure is on the central (lower) side of the gradient. During ventilation, artificial inspiration momentarily increases intrathoracic pressure which results in a short increase of CVP. Inspiration for a short time changes the pressure gradient and the level of remaining flow is driven mainly by the level of stressed volume alone. Flow measured during inspirium is therefore a dynamic indicator of stressed volume level, the primary driver of preload. The following algorithm may be used to calculate surrogate preload: Preload=APVinsp (cm/s)=VTIinsp cm2/time=FLOWinsp ml/time (all within Superior Vena Cava). APVmin is an algorithmic alternative to APVinsp, where APVmin represents heart beat with minimal average peak velocity within respiratory cycle, while APVinsp averaging period is based on length of inspiration. Surrogate preload may also be determined using total retrograde flow (Retrograde VTI/sec), Systolic Wave Peak Velocity, Systolic Wave VTI, and/or AR Wave Peak Velocity, AR Wave VTI.

The computer 22 may calculate a variety of Arterial Pressure (AP) data. For example, Systolic Arterial Pressure may be calculated as an average (max amplitude) over a calculation time period. Diastolic Arterial Pressure may be calculated as an average (min amplitude). Mean Arterial Pressure (MAP) may be calculated using the following algorithm: MAP=Diastolic AP plus (Systolic AP−Diastolic AP)/3. Mean Arterial Pressure may also be calculated as a true Mean of multiple arterial pressure waveform samples acquired during individual heart beat. Pulse Pressure may be calculated by subtracting the Diastolic AP from the Systolic AP. Pulse Pressure Variation (PPV) may be calculated using the following algorithm: PPV=(PPmax−PPmin)/AVG(PPmax:PPmin)×100. Cardiac Output and/or Stroke Volume may be calculated from the Arterial Pressure Waveform, for example, by using the Liljestrand-Zander formula: CO=k* (SBP−DBP)/(SBP+DBP)*HR.

Figure 7:
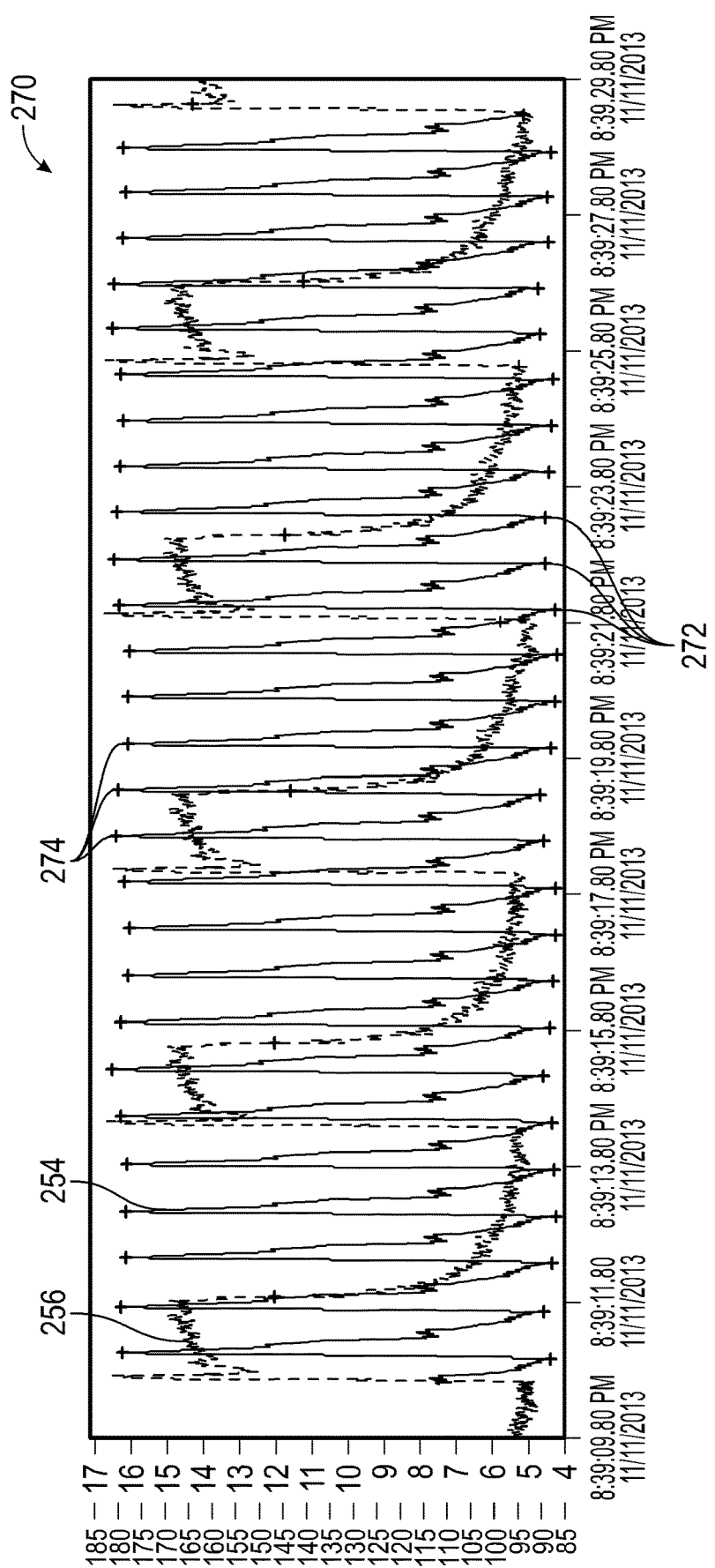
FIG. 7 depicts a screenshot of PPV Index data in accordance with the present disclosure.

In one example of displayed data, FIG. 7 depicts a screenshot 270 of the arterial waveform data for calculation of a Pulse Pressure Variation (PPV) Index. The screenshot 270 again depicts the Doppler flow velocity envelope 254 and the respiration waveform 256. In this example, crosses "+" on the waveforms 254, 256 mark the diastolic pressure 272 and the systolic pressure 274. In one example the diastolic pressure 272 and the systolic pressure 274 are marked with different color crosses. In one example the diastolic pressure 272 is marked with blue color crosses while the systolic pressure 274 is marked with red color crosses. It will be understood that any color or marking may be used so long as the diastolic pressure 272 and systolic pressure 274 are communicated to the user.

In one embodiment, the computer 22 may calculate the value of peaks of systolic waves including systolic retrograde (VR) and systolic antegrade (S) peaks (maximums), the value of individual envelopes (that is, the square size under the contour of the wave) of the systolic waves, the ratio of VR peak to S peak, the ratio of VR envelope to S envelope, indexes based on the ratios such as a Tricuspid Regurgitation Index, and the like.

The computer 22 may output the monitored input hemodynamic data and calculated hemodynamic data in a format to be rendered by the display 18 into indicia that is readable by the user on the display 18. The data may be displayed in real-time or as historical data. Real-time calculations may include, for example, Venous Return Variation Index, Cardiac Output, Preload, Central Venous Pressure, Arterial Pressure, Tricuspid Regurgitation Index, and/or Systemic Vascular Resistance. Of course, it should be understood that more or fewer data calculations may be displayed. Data may be displayed in the form of charts and/or figures. In one embodiment, a user may zoom and pan within the displayed charts and figures.

Figure 8:
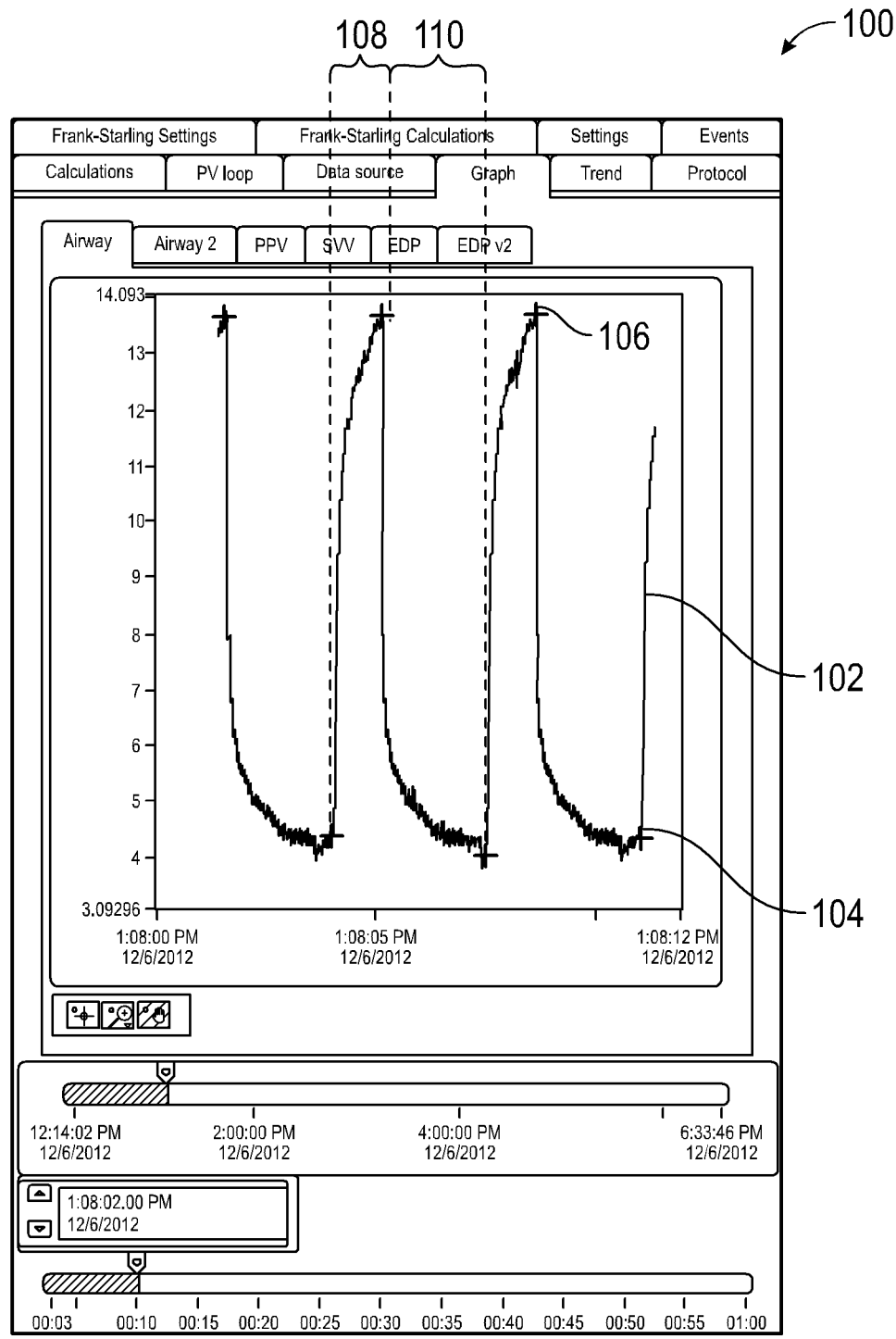
FIG. 8 depicts a screenshot of an exemplary display of a respiration waveform in accordance with the present disclosure.

In one example of displayed data, FIG. 8 depicts a screenshot 100 of an exemplary display in accordance with the present disclosure. As illustrated in FIG. 8, the computer 22 may display a respiration waveform 102 representative of the respiration data. The computer 22 may calculate and/or compare measured values between phases of inspiration in the respiration waveform 102. The computer 22 may utilize processing of the respiration waveform 102 for calculation timing purposes. The example of FIG. 8 represents a respiration waveform of a patient on a respirator, as can be inferred from the regular pattern of inspiration and expiration. In the respiration waveform, the start of the inspiration phase is indicated by bottom point 104 of the wave. The inspiration phase ends at the start of the expiration phase, indicated by top point 106 of the wave. The computer 22 may isolate two phases out of one respiratory cycle—an inspiration time period (Insp) 108 (between the start of the inspiration phase and the end of inspiration phase) and an expiration time period (Exp) 110 (between the start of the expiration phase and the end of the expiration phase).

Figure 9:
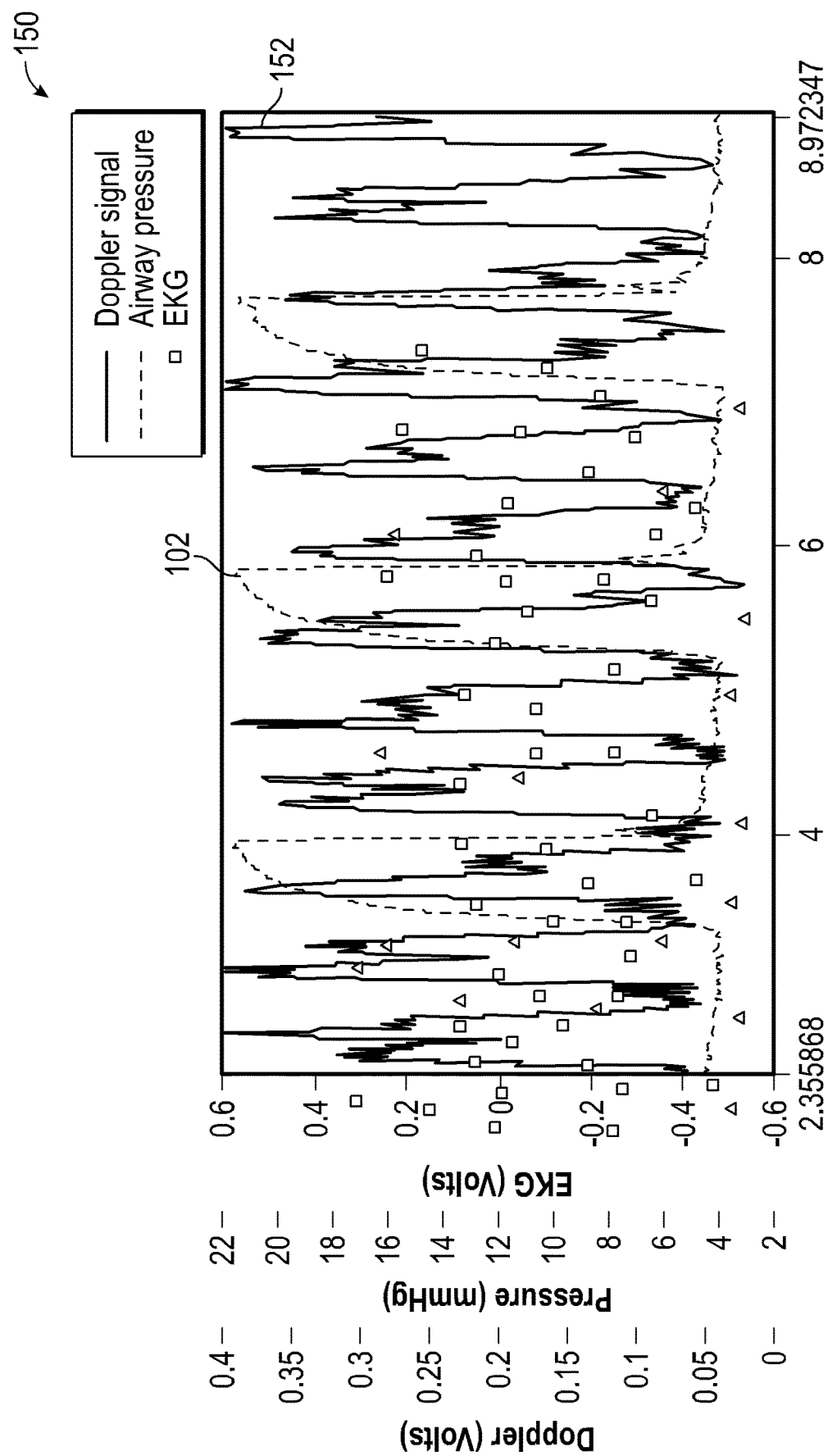
FIG. 9 depicts a screenshot of an exemplary display of waveforms in accordance with the present disclosure.

Additionally, the Doppler data may be displayed as a Doppler velocity waveform representative of velocity over time (cm/s). FIG. 9 depicts a screenshot 150 of another exemplary display in accordance with the present disclosure displaying both an exemplary respiration waveform 102 and an exemplary Doppler velocity waveform 152. The venous system waveform consists of a number of pulse waves occurring within one heartbeat. The most prominent Doppler velocity waveforms 152 are the S-wave (systolic), D-wave (diastolic), and AR wave (right atrium contraction). The computer 22 may isolate the contour of the Doppler velocity waveform, where each sample represents Instant Peak Velocity (IPV) 154. IPV 154 may be used for Doppler algorithmic calculations.

The display of the combination of the respiration waveform 102 and Doppler velocity waveform 152 may provide insight into the patient's fluid responsiveness status. For example, in the screenshot 150 depicted in FIG. 9, the IPVs 154 remain relatively consistent and high compared to the respiration waveform 102 throughout the timeframe. This may indicate that the patient is not fluid responsive. In this example, the fluid responsiveness is +500 mL.

Figure 10:
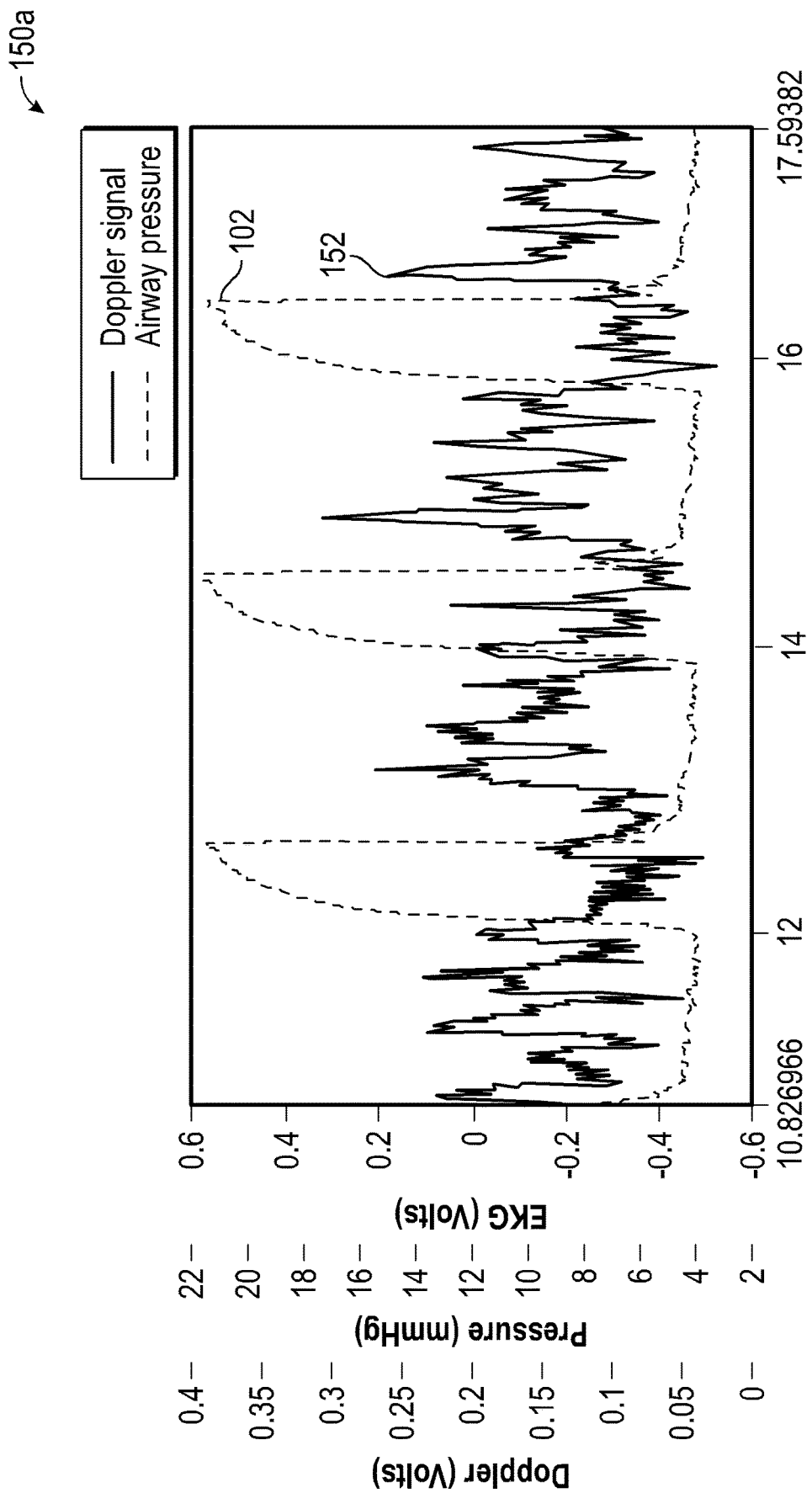
FIG. 10 depicts yet another screenshot of an exemplary display of waveforms in accordance with the present disclosure.

FIG. 10 is an exemplary screenshot 150a of a display of the respiration waveform 102 and Doppler velocity waveform 152 after the same patient lost 30% of the patient's blood. In this example, the overall flow is smaller. The peak velocities are half the velocities of FIG. 9 and the fluid responsiveness is −180 mL. Variation in the Doppler velocity waveform 152 is large between inspiration and expiration in the respiration waveform 102. The Doppler velocity waveform 152 indicates small flow during the first inspiration time period 108a and third inspiration time period 108c. In this example, the Venous Return Variation Index calculated by the computer 22 would be very high.

In one embodiment, an ECG waveform 156 representative of the ECG data may be displayed on display 18. Returning to FIG. 2, for example, FIG. 2 depicts a screenshot 160 of an exemplary display in accordance with the present disclosure displaying an exemplary ECG waveform 156 as well as an exemplary respiration waveform 102 and an exemplary Doppler velocity waveform 152. The screenshot 160 also depicts a Central Venous Pressure waveform 162. One or more of the waveforms 102, 152, 156, 162 may be depicted in different colors for ease of differentiation. Waveforms may be displayed together or in a dedicated chart or any subcombination thereof. Of course, other waveforms may be displayed.

Figure 11:
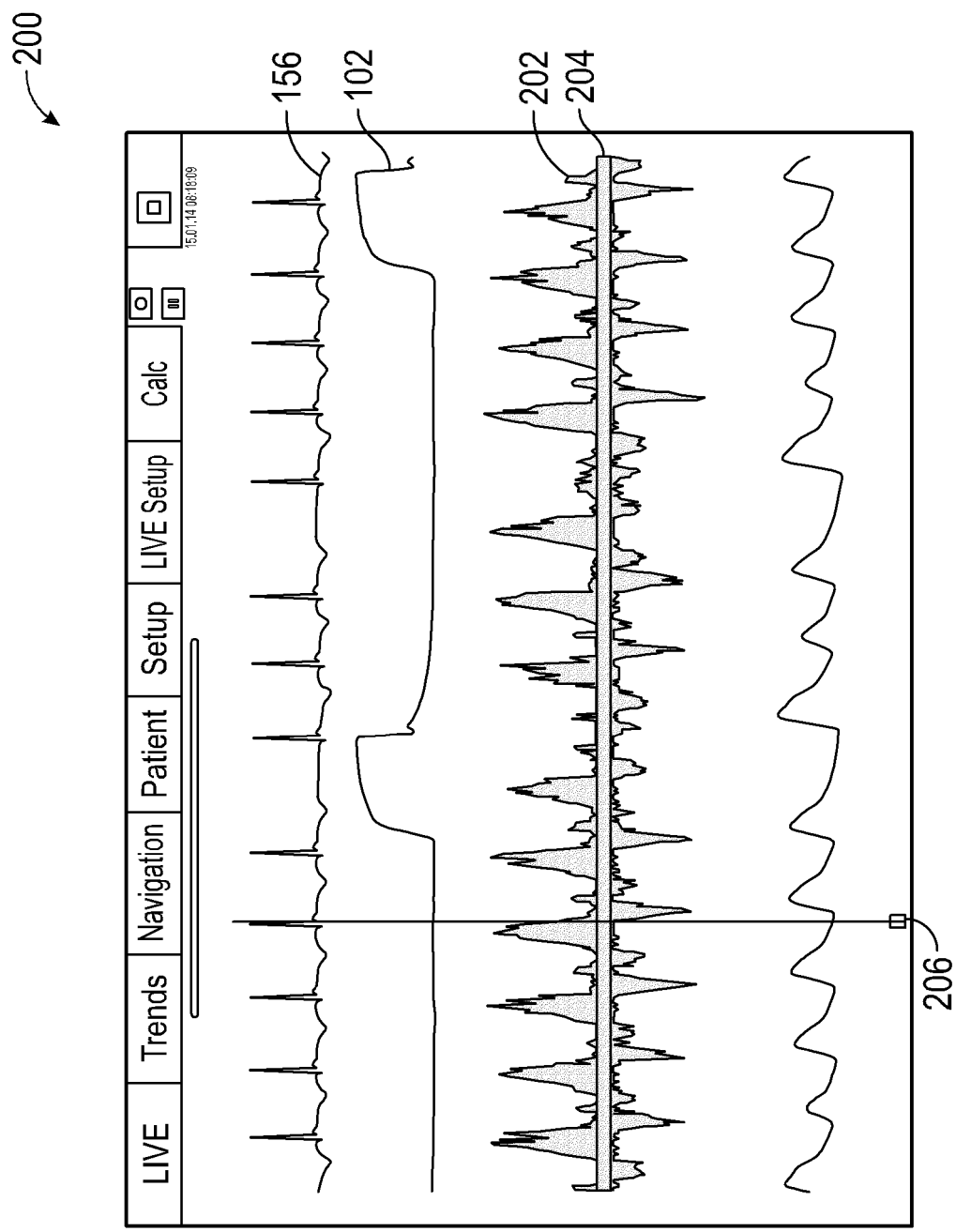
FIG. 11 depicts a screenshot of an exemplary display of a Doppler velocity waveform in accordance with the present disclosure.

FIG. 11 depicts a screenshot 200 of an exemplary display of a Doppler velocity waveform 202 in accordance with the present disclosure. In one embodiment, the Doppler velocity waveform may be indicative of the level of right ventricle dysfunction and/or acute pulmonary hypertension in the patient. The first sensor 26 implemented as an intravascular Doppler probe allows for continuous dynamic assessment of right heart dysfunction through monitoring the flow patterns. In this example, a baseline 204 is established comparatively with the velocity waveform 202 across a timeline (x-axis). The peaks and valleys of the waveform represent antegrade and retrograde waves. The waveform above the baseline 204 is indicative of antegrade flow. The waveform below the baseline 204 is indicative of retrograde flow. Cursor line 206 on the screenshot 200 marks the beginning of Systole. Normally, the antegrade systolic wave should rise to the right from line 206. Instead, a negative wave is shown, and even the positive wave is smaller than would be shown in a normal pattern. Instead, the diastolic antegrade wave dominates the pattern.

In the example depicted in FIG. 11, the data indicates an altered flow pattern in the superior vena cava of the mammalian patient due to right heart dysfunction.

An ECG waveform 156 representative of the ECG data may be utilized in conjunction with the velocity waveform 202. The ECG waveform may be indicative of which waves are systolic waves.

A respiration waveform 102 may also be utilized in conjunction with the velocity waveform 202, however, inspiration and expiration may be estimated based on the velocity waveform 202 pattern.

Figure 12:
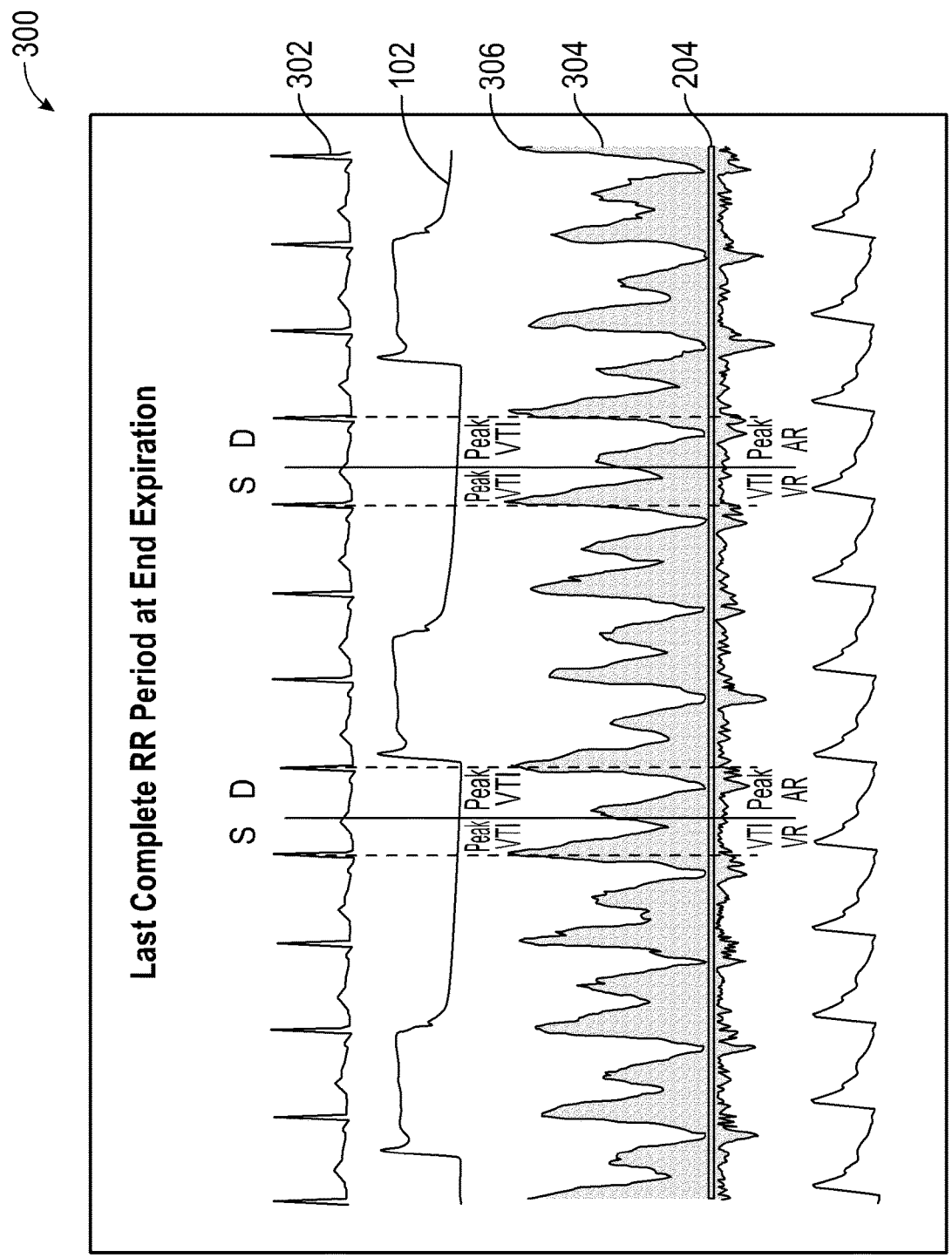
FIG. 12 depicts another screenshot of an exemplary display of a Doppler velocity waveform in accordance with the present disclosure.

FIG. 12 depicts an example of data waveforms which may be displayed on a screenshot 300 in accordance with the present disclosure. The screenshot 300 displays an ECG waveform 302 as well as a normal Doppler velocity waveform 304. The ECG waveform 302 is indicative of which velocity waveforms 304 are systolic (S) and which waveforms 304 are diastolic (D). The velocity waveforms 304 include four types—S, D, VR, and AR. The S wave type is systolic antegrade and the VR wave type is systolic retrograde. The D wave type is diastolic antegrade and the AR wave type is diastolic retrograde. Again, a respiration waveform 102 may also be utilized and/or displayed in conjunction with the velocity waveform 202. The screenshot 300 depicts an example of a typical SVC flow velocity pattern. The individual last full heart beat of every respiration cycle is analyzed with the aid of ECG and Respiration waveforms 302, 102. In this example, dotted lines from the R-peak and T-wave of the ECG waveform 302 indicate systole and diastole, though it will be understood that there are other means through other waveforms (such as Doppler and Arterial Pressure) to indicate the start of systole and diastole. The flow within the analyzed heart beat may be divided into four sections: S (systolic antegrade flow), D (diastolic antegrade flow, VR (systolic retrograde flow), AR (diastolic retrograde flow). An algorithm calculates the flow pattern envelope (the blue waveform, that is, the waveform 306 bordering the Doppler waveform 304). Peak Velocity and Velocity time Integral Values may be calculated out of the Doppler flow envelope in each of the four sections.

In one embodiment, the computer 22 may calculate a variety of data indicative of the level of right ventricle dysfunction and/or acute pulmonary hypertension in the patient. The computer 22 may distinguish the systolic waves/data in the velocity waveforms 304, 306. ECG data and/or ECG waveforms 302 may be indicative of the systolic waves in the velocity waveforms 304, 306. The computer 22 may analyze the systolic waves/data to determine the level of right ventricle dysfunction and/or acute pulmonary hypertension in the patient.

For example, the computer 22 may determine and/or calculate the value of the peaks of the systolic waves including retrograde (VR) and antegrade (S) peaks (maximums), the value of the individual envelopes (that is, the square size under the contour of the wave) of the systolic waves, the ratio of a VR and an S peak, the ratio of a VR envelope and a S envelope, and the like. Typically, for example in ventilated patients, the ratios will be higher during the inspiration phase than during the expiration phase. The respiration waveform may be utilized to determine systolic wave pattern during inspiration and systolic wave pattern which occurs during expiration.

Figure 13:
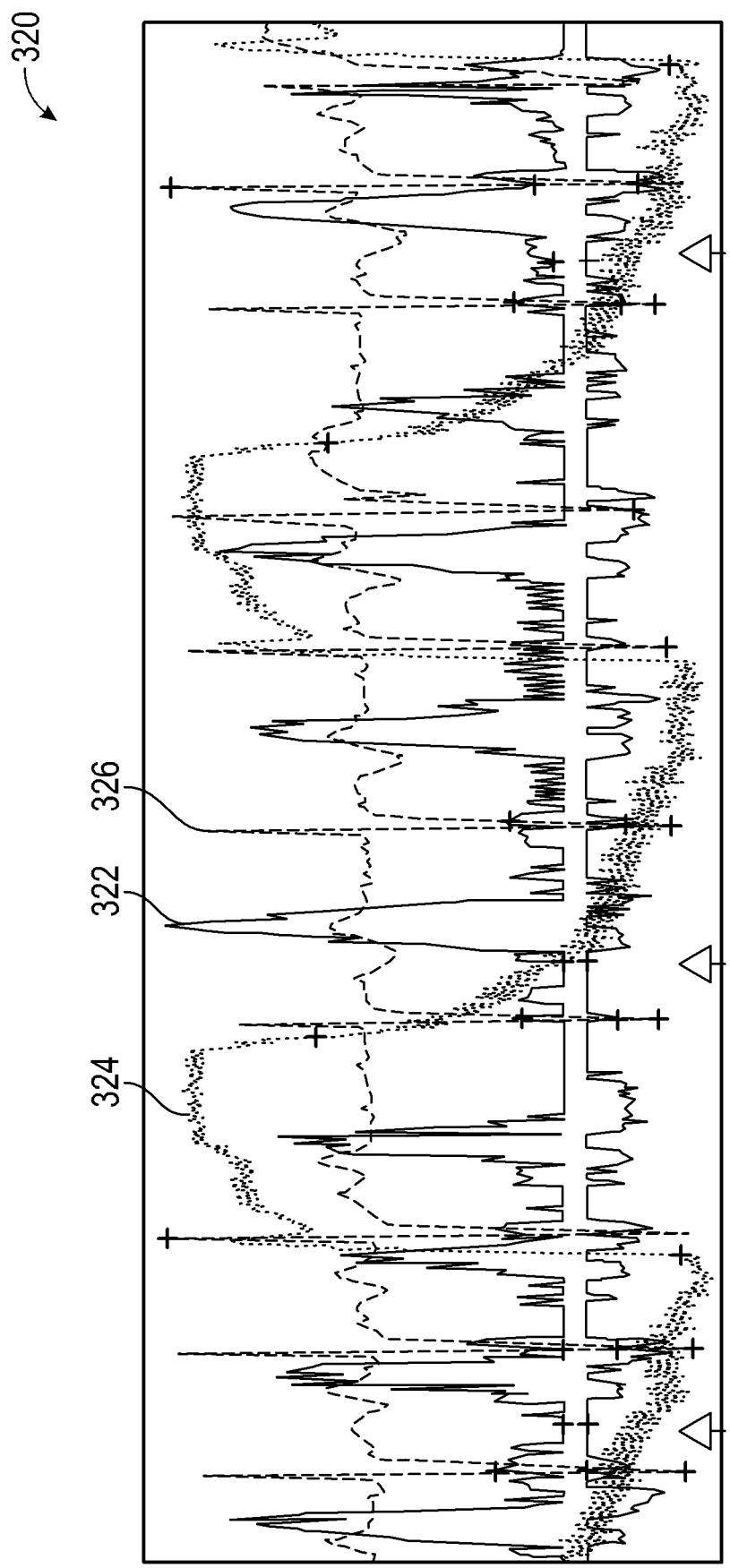
FIG. 13 depicts an example of a screenshot in accordance with the present disclosure displaying waveforms.

FIG. 13 is a screenshot 320 of an Ultrasound Doppler envelope waveform 322, a Respiration waveform 324, and an ECG waveform 326, for analysis in accordance with the inventive concepts disclosed herein. Points on the waveforms may be marked showing the beginning and end of individual respiration cycles, individual heart beat periods (that is, the last complete heartbeat of each expiration), the divide between expected systolic and diastolic Doppler waves, and so on. The Ultrasound Doppler envelope waveform 322 has segments S, D, VR, and AR (as previously described) which may be analyzed for Peaks and Velocity Time Integrals (VTI).

A tricuspid regurgitation (TR) index may be determined as a percentage from the peak and/or envelope ratios from the systolic velocity waveform. The TR index may be determined for the inspiratory phase and the expiratory phase. In one embodiment, the TR index may be calculated utilizing three monitoring modalities—the Doppler velocity waveform from data measured by the first sensor 26 positioned in the superior vena cava, the respiration waveform from data measured by the second sensor 30, and the ECG waveform from data measured by the second sensor 30. The TR index is indicative of the level of right ventricle dysfunction and/or acute pulmonary hypertension in the patient.

Additionally, the computer 22 may use the waveforms to calculate additional data. For example, the computer 22 may calculate averages by calculating the area under the waveform curve for different time periods.

Figure 14:
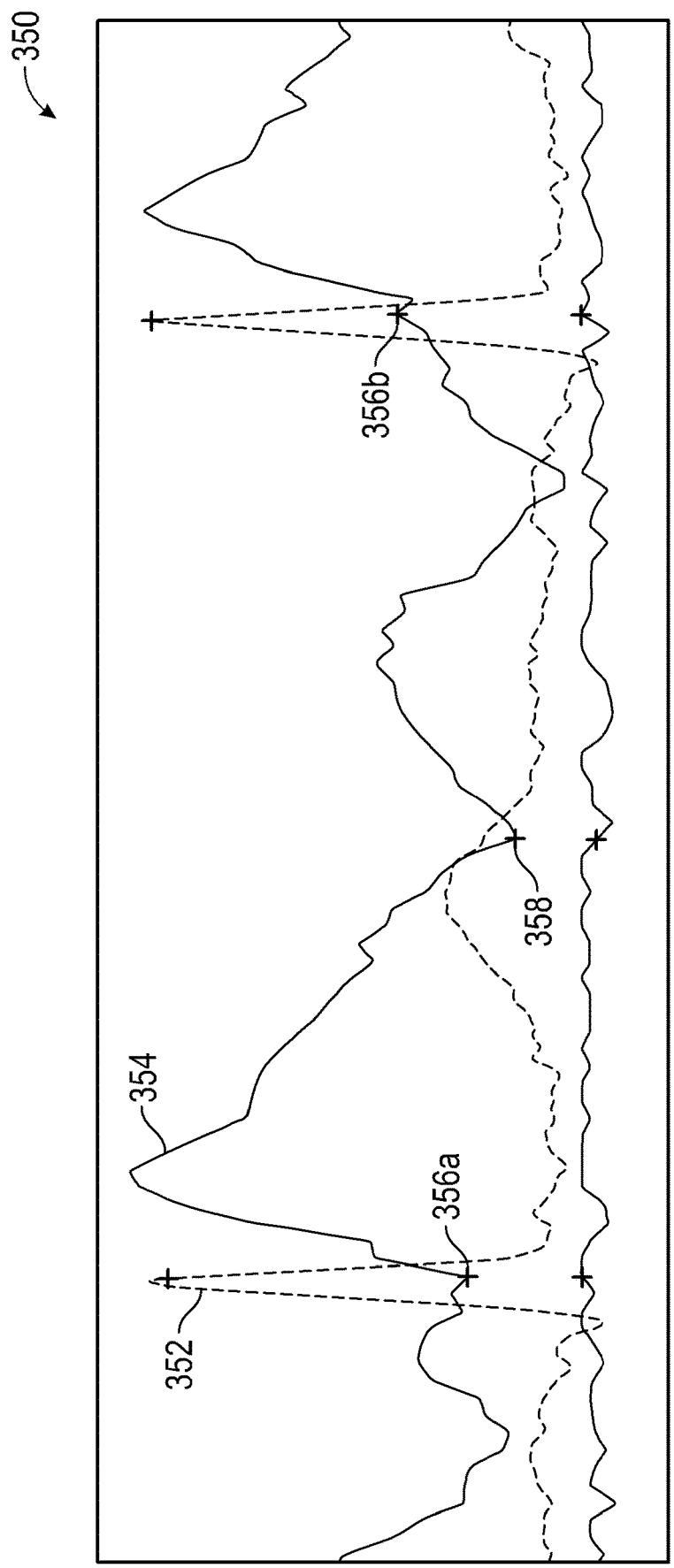
FIG. 14 depicts an example of a screenshot displaying waveform with point analysis in accordance with the present disclosure.

FIG. 14 is an exemplary screenshot 350 of data analysis of a single heart beat for calculation of an SD Index. The SD Index is the ratio between the peak velocity of systolic and diastolic waves. In this example, line 352 represents data derived from ECG data, line 354 represents data derived from ECG and Doppler envelope data, points 356a and 356b represent the beginning of the systolic period, and point 358 marks the beginning of the diastolic period. The systolic wave peak velocity is higher than the diastolic wave peak velocity in this example, as can be seen by the peaks of line 354. Both waves are present. An optimal ratio for a normal SVC flow pattern may be approximately between 1.2 and 1.8. Typically, normal flow is present in the absence of right heart dysfunction and when venous return is optimal.

Figure 15:
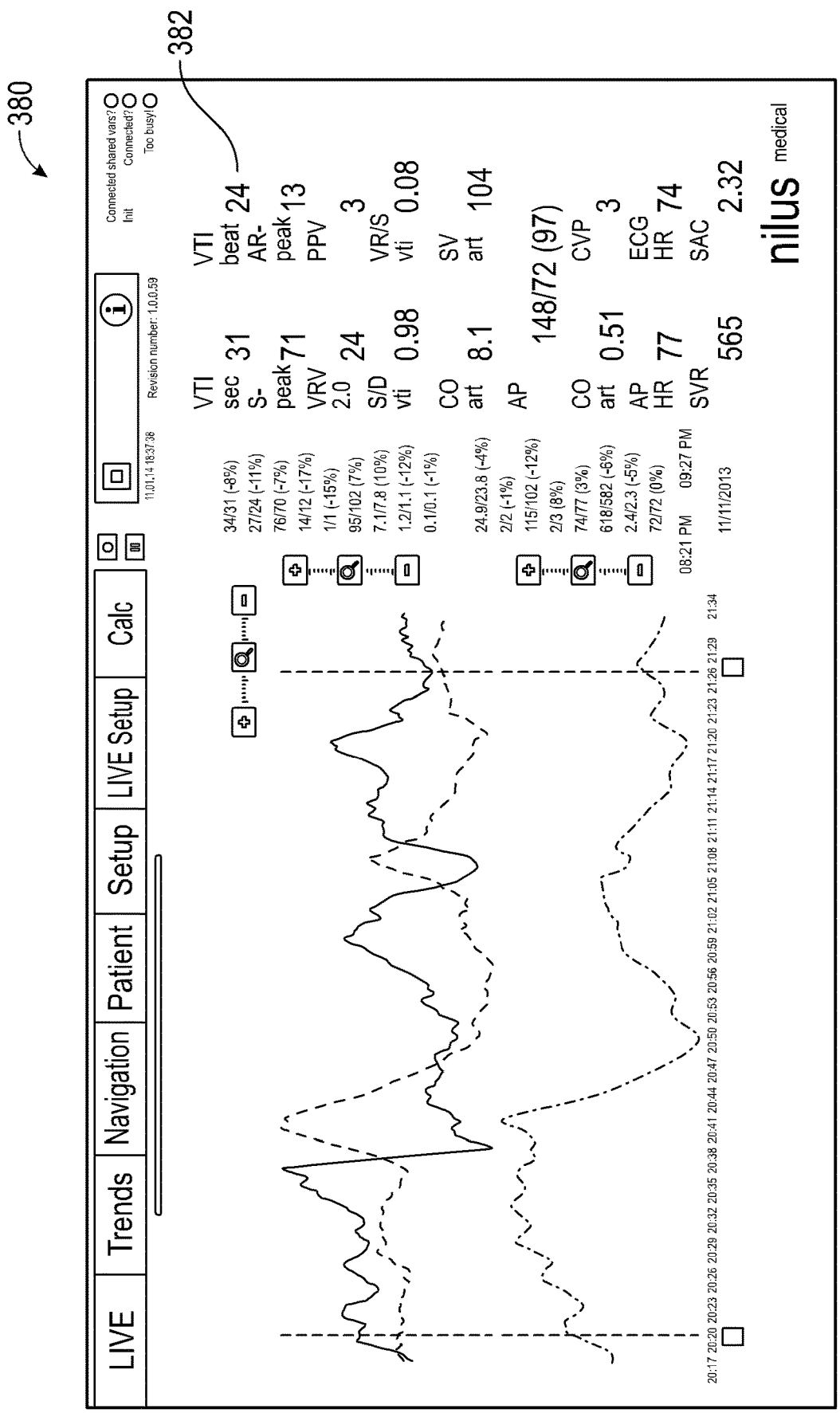
FIG. 15 depicts a screenshot of an exemplary display of trend data in accordance with the present disclosure.

FIG. 15 is an exemplary screenshot 380 of a trend chart in accordance with the present disclosure. In one embodiment, the computer 22 may display data in one or more trend charts. In the example of FIG. 15, Stroke Volume, Preload and Venous Return Variation Index are displayed. Data indicative of blood responsiveness may be overlaid on the trend charts, such as those shown in data 382. Of course, any input data or calculated data may be displayed on trend charts. One example is a trend chart displaying SVC VTI/beat versus APVinsp. The trend lines may be in different colors.

The VRV Index may be indicative of fluid responsiveness of the patient. The APVinsp alone may correlate well with other preload markers, for example, a lower APVinsp means lower preload. A user, such as a Clinician, may look at both VRV index and APVinsp to assess the level of volemia. The APVinsp may also be examined in relationship with Stroke Volume. Additionally, or alternatively, a user may look at VTImin, VTI-R (retrograde), and/or Systolic Wave peak or VTI In one embodiment, the user may select data options for trend chart creation. For example, real-time or historic trend charts may be created by the computer 22 for the data. Exemplary data for trend charts includes, but is not limited to, Cardiac Output, Cardiac Index, Venous Return, SVCvti, APVinsp, VRV Index, MAP, and CVP. The user may be given the option to select between trend charts displayed for data in "per minute" values or "per beat" values, where applicable. Data may be combined to show multiple trends on one chart, with individual scales per data type indicated on the chart axes. The system may offer the option to smooth trends in trend charts by moving average value selection. Additionally, one or more timeline cursors and/or other cursors may be available for the user. The system may also provide the user the ability to display events on the timeline of the trend charts and/or input specific patient information into the charts.

Figure 16:
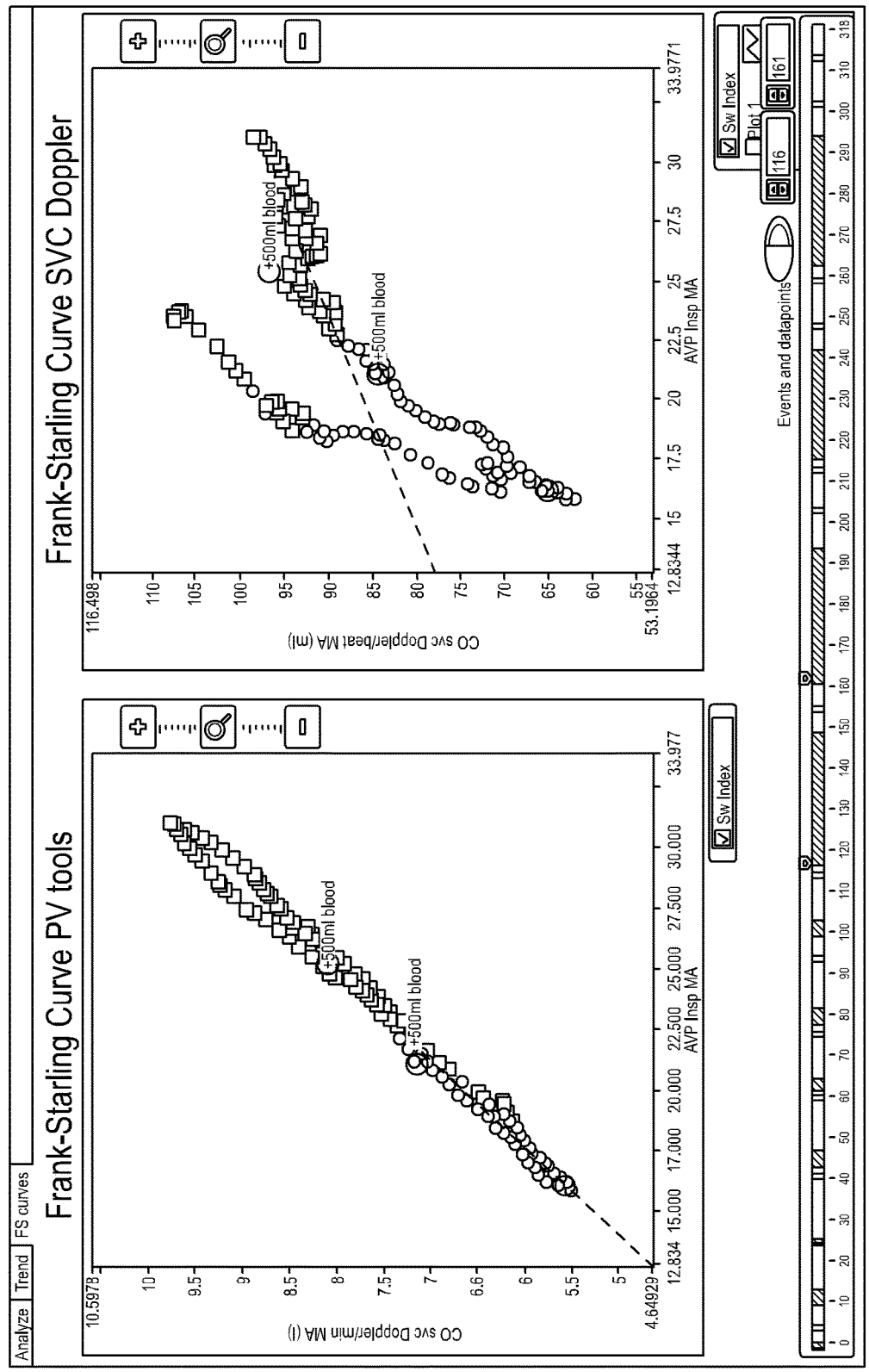
FIG. 16 depicts a screenshot of an exemplary display of Frank-Starling curves in accordance with the present disclosure.

Another example of data displays are Frank-Starling charts (APVinsp . . . x axes, SVC vti . . . y axes), as depicted in the exemplary screenshot 400 of a display in FIG. 16. The user may be provided with the option to show data as per minute or per beat on the Frank-Starling charts. The user may utilize the Frank-Starling charts to help determine hemodynamic parameters and status of the mammalian patient. The Frank-Starling curve may flatten if too much fluid is administered to the patient. The computer 22 may alert the user, for example, audibly, when too much fluid is administered. The Frank-Starling curve may be represented by one or more colors. For example, a change in color may indicate VRV threshold of 13%. The display may be provided with an embedded Systematic Vascular Resistance chart such that a user may access the Systematic Vascular Resistance chart while viewing the Frank-Starling Chart. The Systematic Vascular Resistance chart may have MAP-CVP (or MAP) charted against CO.

In one example, the computer 22 may display data as one or more Systemic Vascular Resistance chart (MAP-CVP . . . x axes, SVC vti . . . y axes).

In one embodiment, the display 18 may be used to monitor patient status in real-time. For example, a Live Screen mode may be used to display running real-time charts for data and calculations such as ECG lead II, ECG intravascular lead, Ultrasound Doppler with Respiration waveforms, Arterial Pressure, and/or Central Venous Pressure. In one example, the running charts may display a certain amount of past data, such as the latest 10 seconds of one or more of the waveforms. The Live Screen may also display charts of data and/or selected calculated parameters. The Live Screen may also contain an option to record ECG waveforms and Doppler waveforms 152 in a screenshot. The option may be in the form of a "button" for the user to select, such as a "Catheter Tip Position Confirmation" button. The Live Screen may also include a START/STOP button with which the user may trigger recording and displaying of trend calculation and waveforms.

In one embodiment, the computer 22 may alert the user when hemodynamic parameters reach a predetermined threshold. For example, the computer 22 may cause the display 18 to alert the user visually and/or audibly when the TR index(es), or the peak ratio(s), or the envelope ratio(s), indicative of the level of right ventricle dysfunction and/or acute pulmonary hypertension in the patient, reach a predetermined threshold level. The threshold level may be determined by the user. Visual alerts may be, for example, a different color for the waveform/data and/or pop-up messages on the display.

The computer 22 may execute software to create and export data files based on the data input and/or calculations. Some non-exclusive examples of data files include Clinical Procedure Reports, Trends, Charts, Events Data, Raw data, Screenshots (such as waveforms or charts), Video of recorded real-time data displays, and/or combinations thereof. The data files may be stored in memory 54 and/or exported, for example, using a network, external memory, and/or hard copy.

The system may provide the user with options for monitoring data. For example, a variety of different data charts and data charts in combination with waveforms may be available as options for hemodynamic monitoring on the display 18 and/or in reports. In one example, an "ECG lead II" option may be available with a chart showing the ECG waveform. The ECG waveform may have a color, for instance, green. The heart rate value may be displayed ("HR xx") with the chart. The heart rate value may be displayed in the same color as the ECG waveform for ease of discernment.

As another example, an "ECG intravascular lead" option may be available showing an intravascular ECG waveform. In this example, the p-wave may be highlighted, for example, in color, such as blue. In this example, the chart the "Catheter Tip Confirmation" button may be located next to the waveform chart.

In yet another example, an "Ultrasound Doppler with Respiratory waveform" chart may be available, as previously described in conjunction with FIGS. 9 and 10. In this example, the user may have the option to display parameters with the waveform chart, such as APVinsp (Average Peak Velocity during inspiration) and/or VRV (Venous Return Variation Index). Again, the waveforms and parameters may be color coded. The system may allow a user to select options in a "setup" mode for which data is to be displayed. Some exemplary options include, but are not limited to, (SVCvti/min and SVCvti/beat); (VR and VR/beat), (CO and SV), and/or (CI and SI). The same options may be available for setup of the Frank-Starling charts previously described in conjunction with FIG. 16.

In another example, an "Arterial Pressure" chart may be available. The Arterial Pressure chart may display an Arterial pressure waveform. The waveform may be a color, such as red. Parameters may be displayed with the chart, such as Systolic/Diastolic Pressure (Mean Arterial Pressure) . . . 120/80 (95).

In another example, a "Central Venous Pressure" chart may be available. The Central Venous Pressure chart may display a Central Venous Pressure waveform. The waveform may be a color, such as blue. Parameters may be displayed with the chart, such as CVP max/CVP min (CVP) . . . 10/2 (6).

In another example, the computer 22 may display a combination of charts and "gauges" where the gauges are indicative of data for specific data inputs and/or calculated data. For example, gauges may be indicative of Cardiac Output, Preload (APVinsp), VRV Index, MAP, CVP, SVR, TR Index, etc. In one example, the gauges may display optimal ranges for the data.

Of course, it should be understood that other charts and parameters and/or combinations may be available to the user on the display 18 and/or in report/export format.

CONCLUSION

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

The invention claimed is:

1. A hemodynamic monitoring device, comprising:
a first sensor configured to measure a velocity of blood flow in a superior vena cava of a mammalian patient using ultrasound waves, wherein the first sensor comprises an intravascular Doppler probe configured to provide an instant peak velocity of blood flow at one or more discrete measurement times;
a second sensor configured to measure respiratory cycle data of the mammalian patient;
an input for receiving the measured velocity of blood flow and the measured respiratory cycle data; and
a computer configured to dynamically:
process the measured velocity of blood flow and the measured respiratory cycle data to provide hemodynamic parameters corresponding to the mammalian patient, wherein processing of the measured velocity of blood flow from the intravascular Doppler probe includes determining an average instant peak velocity during an inspiration time period (APVinsp) and an average instant peak velocity during an expiration time period (APVexp), and wherein processing the measured respiratory cycle data comprises determining at least one respiratory waveform having the inspiration time period and the expiration time period;
determine a sequence of points indicative of ratios between the APVinsp and APVexp for multiple respiratory waveforms for a period of time;
determine a relative slope for a line through the sequence of points; and
indicate to a user at least one of:
that the mammalian patient is fluid responsive when the relative slope is above a predetermined level; and
that the mammalian patient is fluid non-responsive when the relative slope is below the predetermined level.

2. The device of claim 1, wherein the second sensor comprises at least one of a respiratory airway pressure transducer assembly and an electrocardiographic (ECG) assembly configured to provide bioimpedance measurements of a chest wall of the mammalian patient.

3. The device of claim 1, wherein the device includes a display configured to display at least one of the following: the measured velocity of blood flow, the measured respiratory cycle data, the hemodynamic parameters in real-time, the hemodynamic parameters continuously, the measured velocity of blood flow, the measured respiratory cycle data, and the hemodynamic parameters as trended over time.

4. The device of claim 1, wherein the first sensor is configured to measure velocity of blood flow using at least one of continuous-wave or pulse-wave Doppler ultrasound.

5. The device of claim 1, wherein the computer is configured to indicate to the user at least one of:
that the mammalian patient is fluid responsive when the relative slope is above the predetermined level and when a Venous Return Variation (VRV) Index is above a predetermined number; and
that the mammalian patient is fluid non-responsive when the relative slope is below the predetermined level and when the Venous Return Variation (VRV) Index is below the predetermined number.

6. The device of claim 5, wherein the Venous Return Variation (VRV) Index is determined using the following, where APVmin is a smallest APV, and APVmax is a largest APV out of every respiratory cycle:

$$VRV = (APVmax - APVmin)/Average(APVmax: APVmin) \times 100.$$

7. The device of claim 1, wherein the first sensor is configured to measure the velocity of blood flow continuously in real-time and the second sensor is configured to measure respiratory cycle data continuously in real-time.

8. A hemodynamic monitoring device, comprising:
a first sensor configured to measure a velocity of blood flow in a superior vena cava of a mammalian patient using ultrasound waves, wherein the first sensor comprises an intravascular Doppler probe configured to provide an instant peak velocity of blood flow at one or more discrete measurement times;
a second sensor configured to measure respiratory cycle data of the mammalian patient;
an input for receiving the measured velocity of blood flow and the measured respiratory cycle data; and
a computer configured to dynamically:
process the measured velocity of blood flow and the measured respiratory cycle data to provide hemodynamic parameters corresponding to the mammalian patient, wherein processing the measured respiratory cycle data comprises determining at least one respiratory waveform having an inspiration time period and an expiration time period;
determine a sequence of points indicative of ratios between corresponding stroke volumes of a heart of the mammalian patient and Average Peak Velocity (APV) for multiple respiratory waveforms for a period of time;
determine a relative slope for a line through the sequence of points; and
indicate to a user at least one of:
that the mammalian patient is fluid responsive when the relative slope is above a predetermined level; and
that the mammalian patient is fluid non-responsive when the relative slope is below the predetermined level.

9. The device of claim 8, wherein the first sensor is configured to measure the velocity of blood flow continuously in real-time and the second sensor is configured to measure respiratory cycle data continuously in real-time.

10. A hemodynamic monitoring device, comprising:
a first sensor configured to measure a velocity of blood flow in a superior vena cava of a mammalian patient using ultrasound waves, wherein the first sensor comprises an intravascular Doppler probe configured to provide an instant peak velocity of blood flow at one or more discrete measurement times;
a second sensor configured to measure respiratory cycle data of the mammalian patient;
an input for receiving the measured velocity of blood flow and the measured respiratory cycle data; and a computer configured to dynamically:
  process the measured velocity of blood flow and the measured respiratory cycle data to provide hemodynamic parameters corresponding to the mammalian patient, wherein processing the measured respiratory cycle data comprises determining at least one respiratory waveform having an inspiration time period and an expiration time period, and wherein processing the measured velocity of blood flow from the intravascular Doppler probe includes determining a systolic portion of the measured velocity of the blood flow, including systolic antegrade and systolic retrograde blood flow during the inspiration time period and during the expiration time period;
  determine at least one of:
    peak velocities of the systolic antegrade and systolic retrograde blood flow, the computer configured to determine a tricuspid regurgitation index based at least in part on the determined peak velocities of the systolic antegrade and systolic retrograde blood flow; and
    the value of a square area under a waveform of the systolic antegrade and the value of a square area under a waveform of the systolic retrograde blood flow, the computer configured to determine a tricuspid regurgitation index based at least in part on the values of the square areas;
  indicate to a user at least one of:
    that the mammalian patient is at least one of having tricuspid regurgitation or not having tricuspid regurgitation based at least in part upon the tricuspid regurgitation index;
    that the mammalian patient is having tricuspid regurgitation when the tricuspid regurgitation index is above a predetermined level; and
    that the mammalian patient is not having tricuspid regurgitation when the tricuspid regurgitation index is below the predetermined level;
  determine a right ventricle dysfunctional state of the mammalian patient based on the hemodynamic parameters; and
  output to the user at least one of visual indicia and audio communications representing the right ventricle dysfunctional state of the mammalian patient based on the hemodynamic parameters.

11. The hemodynamic monitoring device of claim 10, wherein the computer is configured to determine the right ventricle dysfunctional state of the mammalian patient based on the tricuspid regurgitation index.

12. The hemodynamic monitoring device of claim 10, wherein the computer is configured to dynamically:
  determine ratios between systolic wave peak velocities and diastolic wave peak velocities; and
  determine the right ventricle dysfunctional state of the mammalian patient based on the determined ratios between systolic wave peak velocities and diastolic wave peak velocities.

13. The hemodynamic monitoring device of claim 10, wherein the right ventricle dysfunctional state of the mammalian patient is determined and output in real-time.

14. The hemodynamic monitoring device of claim 10, wherein the computer is configured to process the measured velocity of blood flow and the measured respiratory cycle data continuously in real-time.

15. The hemodynamic monitoring device of claim 14, wherein the first sensor is configured to measure the velocity of blood flow continuously in real-time and the second sensor is configured to measure respiratory cycle data continuously in real-time.

* * * * *